US010335491B2

(12) United States Patent
Tseng et al.

(10) Patent No.: US 10,335,491 B2
(45) Date of Patent: Jul. 2, 2019

(54) CATALYTIC DELIVERY NANOSUBSTRATES (CDNS) FOR HIGHLY EFFICIENT DELIVERY OF BIOMOLECULES

(75) Inventors: Hsian-Rong Tseng, Los Angeles, CA (US); Hao Wang, Los Angeles, CA (US); Kuan-Ju Chen, Los Angeles, CA (US)

(73) Assignees: The Regents of the University of California, Oakland, CA (US); National Institutes of Health (NIH), Bethesda, MD (US)

( * ) Notice: Subject to any disclaimer, the term of this patent is extended or adjusted under 35 U.S.C. 154(b) by 29 days.

(21) Appl. No.: 14/234,321

(22) PCT Filed: Jul. 23, 2012

(86) PCT No.: PCT/US2012/047881
§ 371 (c)(1),
(2), (4) Date: Jan. 22, 2014

(87) PCT Pub. No.: WO2013/013245
PCT Pub. Date: Jan. 24, 2013

(65) Prior Publication Data
US 2014/0186426 A1    Jul. 3, 2014

Related U.S. Application Data

(60) Provisional application No. 61/510,263, filed on Jul. 21, 2011.

(51) Int. Cl.
*A61K 47/40*    (2006.01)
*A61K 47/59*    (2017.01)
(Continued)

(52) U.S. Cl.
CPC ............. *A61K 47/59* (2017.08); *A61K 47/54* (2017.08); *A61K 47/595* (2017.08); *A61K 47/60* (2017.08);
(Continued)

(58) Field of Classification Search
None
See application file for complete search history.

(56) References Cited

U.S. PATENT DOCUMENTS 7,579,077 B2    8/2009  Dubrow et al.
8,357,377 B2 *  1/2013  Pun ..................... A61K 9/0014
                                              424/172.1
(Continued)

FOREIGN PATENT DOCUMENTS

WO    WO-2008/133755 A2    11/2008
WO    WO-2009/105662 A1     8/2009
(Continued)

OTHER PUBLICATIONS

Aw et al., Polymeric micelles in porous and nano tubular implants as a new system for extended delivery of poorly soluble drugs. J. Mater. Chem., 2011, 21 , 7082-9.*
(Continued)

*Primary Examiner* — Kevin K Hill
*Assistant Examiner* — Arthur S Leonard
(74) *Attorney, Agent, or Firm* — Venable LLP; Henry J. Daley; Miguel A. Lopez

(57) ABSTRACT

This invention relates, e.g., to a molecular delivery system comprising A. a substrate having a nanostructured surface region which comprises a plurality of nanostructures and, covalently attached to the substrate, multiple copies of a first member of a binding pair; and B. at least one vector nanoparticle which comprises, encapsulated therein, a molecule of interest, and on its surface, multiple copies of
(Continued)

second member of the binding pair. Methods of using the molecular delivery system to deliver a molecule of interest to a cell are also described.

14 Claims, 11 Drawing Sheets

(51) Int. Cl.
| | |
|---|---|
| C12N 15/87 | (2006.01) |
| A61K 48/00 | (2006.01) |
| B82Y 5/00 | (2011.01) |
| A61K 47/60 | (2017.01) |
| A61K 47/54 | (2017.01) |
| A61K 47/69 | (2017.01) |

(52) U.S. Cl.
CPC ...... *A61K 47/6923* (2017.08); *A61K 47/6925* (2017.08); *A61K 47/6951* (2017.08); *A61K 47/6957* (2017.08); *A61K 48/0008* (2013.01); *B82Y 5/00* (2013.01); *C12N 15/87* (2013.01)

(56) References Cited

U.S. PATENT DOCUMENTS

| | | | |
|---|---|---|---|
| 9,140,697 B2 | 9/2015 | Tseng et al. | |
| 2006/0275371 A1 | 12/2006 | Dai et al. | |
| 2008/0177378 A1* | 7/2008 | Asgari | A61L 27/427 623/1.38 |
| 2009/0087493 A1 | 4/2009 | Dai et al. | |
| 2009/0220561 A1* | 9/2009 | Jin | A61K 9/0009 424/423 |
| 2009/0298067 A1 | 12/2009 | Irimia et al. | |
| 2012/0094382 A1 | 4/2012 | Park et al. | |

FOREIGN PATENT DOCUMENTS

| | | |
|---|---|---|
| WO | WO-2010/099466 A2 | 9/2010 |
| WO | WO-2010/108003 A2 | 9/2010 |

OTHER PUBLICATIONS

University of Arizona, Biochem Lecture Slides p. 1-11., 2003. http://cbc.arizona.edu/classes/bioc462/462a/NOTES/CARBO/carb_function.htm.*
Kalyankar et al., Arraying of Intact Liposomes into Chemically Functionalized Microwells. Langmuir 2006, 22, 5403-5411.*
Machut-Binkowski, C.; Hapiot, F.; Cecchelli, R.; Martin, P.; Monflier, E. A versatile liposome/cyclodextrin supramolecular carrier for drug delivery through the blood-brain barrier. J. Incl. Phenom. Macrocycl. Chem. 2007, 57, 567-572.*
Park et al., Tunable Fluorescent Dendron-Cyclodextrin Nanotubes for Hybridization with Metal Nanoparticles and Their Biosensory Function. Angew. Chem. Int. Ed. 2008, 47, 9922-9926.*
Lim et al., DNA-embedded Au/Ag core—shell nanoparticles. Chem. Commun., 2008, 42:5312-5314. (Year: 2008).*
Kwon et al., "Label-free, microfluidic separation and enrichment of human breast cancer cells by adhesion difference" Lab on a Chip, Nov. 7, 2007, vol. 7, No. 11, pp. 1461-1468, ISSN 1473-0197. See Abstract; Figures 1 and 4.
International Search Report dated Jan. 24, 2013, issued in International Application No. PCT/US2012/047881.
Pathak et al., "Drug Delivery Nanoparticles Formulation and Characterization", Informa Healthcare, vol. 191. (2009).
Wang et al., "Three-Dimensional Nanostructured Substrates Toward Efficient Capture of Circulating Tumor Cells", Angewandte Chemie International Edition in English, vol. 48(47), pp. 8970-8973. (2009).
Shalek et al., "Vertical Silicon Nanowires as a Universal Platform for Delivering Biomolecules Into Living Cells", Proceedings of the National Academy of Sciences, vol. 7, No. 5, pp. 1870-1875. (2010).

Podolak, "Nanowire Platform Introduces Biomolecules Into Living Cells", Biotechniques—he International Journal of Life Science Methods. Jan. 15, 2010.
Yum et al., Bio-Functionalized Nanoneedles for the Direct and Site-Selective Delivery of Probes Into Living Cells, Biochimica et Biophysica Acta, vol. 1810, No. 3, pp. 330-338. (2011).
Boukany et al. Nanochannel electroporation delivers precise amounts of biomolecules into living cells. Nat. Nanotechnol. (2011) 6, 747-754.
Cartier et al. Hematopoietic stem cell gene therapy with a lentiviral vector in X-linked adrenoleukodystrophy. Science (2009) 326, 818-823.
Chen et al., Geometric control of cell life and death. Science (1997) 276, 1425-1428.
Chen et al. A small MRI contrast agent library of gadolinium(III)-encapsulated supramolecular nanoparticles for improved relaxivity and sensitivity. Biomaterials (2011) 32, 2160-2165.
Chen et al. The therapeutic efficacy of camptothecin-encapsulated supramolecular nanoparticles. Biomaterials (2012) 33, 1162-1169.
Davis et al., Nanoparticle therapeutics: an emerging treatment modality for cancer. Nat Rev Drug Discovery (2008) 7, 771-782.
De et al., Applications of Nanoparticles in Biology. Adv Mater (2008) 20, 4225-4241.
Donahue, R.E., et al. Stimulation of haematopoiesis in primates by continuous infusion of recombinant human GM-CSF. Nature (1986) 321, 872-875.
Fischer et al. Biomimetic nanowire coatings for next generation adhesive drug delivery systems. Nano Lett (2009) 9, 716-720.
Frank, et al. Investigation of the cause of death in a gene-therapy trial. N. Engl. J. Med. (2009) 361, 161-169.
Hernot et al., Microbubbles in ultrasound-triggered drug and gene delivery. Adv Drug Deliv Rev (2008) 60, 1153-1166.
Iyer et al., Two-step transcriptional amplification as a method for imaging reporter gene expression using weak promoters. P Natl Acad Sci USA. 2001;98(25):14595-600.
Izpisua Belmonte et al., Induced pluripotent stem cells and reprogramming: seeing the science through the hype. Nat rev. Genetics (2009) 10, 878-883.
Jaenisch et al. In vitro reprogramming of fibroblasts into a pluripotent ES-cell-like state. Nature (2007) 448, 318-U312.
Jaiswal et al., Use of quantum dots for live cell imaging. Nat Methods (2004) 1, 73-78.
Kay et al., In vivo gene therapy of hemophilia B: sustained partial correction in factor IX-deficient dogs. Science (1993) 262, 117-119.
Kim et al., Interfacing silicon nanowires with mammalian cells. J Am Chem Soc (2007) 129,7228-7229.
Li et al., Gene therapy progress and prospects: non-viral gene therapy by systemic delivery. Gene. Then: (2006) 13, 1313-1319.
Liu et al., Delivery of intact transcription factor by using self-assembled supramolecular nanoparticles. Angew Chem Int Ed Engl (2011) 50, 3058-3062.
Mehier-Humbert et al., Physical methods for gene transfer: improving the kinetics of gene delivery into cells. Adv. Drug Deliv Rev (2005) 57, 733-753.
Okita et al., Generation of germline-competent induced pluripotent stem cells. Nature (2007) 448, 313-317.
Patil et al., DNA-based therapeutics and DNA delivery systems: a comprehensive review. AAPSJ (2005) 7, E61-77.
Peng et al., Synthesis of large-area silicon nanowire arrays via self-assembling nanoelectrochemistry. Adv Mater (2002) 14, 1164-1167.
Petros et al., Strategies in the design of nanoparticles for therapeutic applications. Nat. Rev. Drug Discov. (2010) 9, 615-627.
Petter et al., Cooperative Binding by Aggregated Mono-6-(Alkylamino)-Beta-Cyclodextrins. JAC S 112(10). (1990):3860-3868.
Pfisterer, U., et al. Direct conversion of human fibroblasts to dopaminergic neurons. *Proc Nati Acad Sci USA* (2011) 108, 10343-10348.
Plath, K. & Lowry, W.E. Progress in understanding reprogramming to the induced pluripotent state. Nat. Rev. Genet. (2011) 12, 253-265.

(56) References Cited

OTHER PUBLICATIONS

Scheiblhofer, S., et al. Gene gun immunization with clinically relevant allergens aggravates allergen induced pathology and is contraindicated for allergen immunotherapy. Mol. Immunol. (2007) 44, 1879-1887.

Sekine, J., et al. Functionalized conducting polymer nanodots for enhanced cell capturing: the synergistic effect of capture agents and nanostructures. Adv Mater (2011) 23, 4788-4792.

Shalek, A.K., et al. Vertical silicon nanowires as a universal platform for delivering biomolecules into living cells. Proc Natl Acad Sci USA (2010) 107, 1870-1875.

Vierbuchen, T., et al. Direct conversion of fibroblasts to functional neurons by defined factors. Nature (2010) 463, 1035-1041.

Wang, H., et al. A rapid pathway toward a superb gene delivery system: programming structural and functional diversity into a supramolecular nanoparticle library. ACS Nano (2010) 4, 6235-6243.

Wang, H., et al. A small library of DNA-encapsulated supramolecular nanoparticles for targeted gene delivery. Chem Commun (Camb) (2010) 46, 1851-1853.

Wang, H., et al. A supramolecular approach for preparation of size-controlled nanoparticles. Angew Chem Int Ed Engl (2009) 48, 4344-4348.

Wang, S., et al. Photothermal effects of supramolecularly assembled gold nanoparticles for the targeted treatment of cancer cells. Angew Chem Int Ed Engl (2010) 49, 3777-3781.

Woods, N.B., Bottero, V., Schmidt, M., von Kalle, C. & Verma, Therapeutic gene causing lymphoma. Nature (2006) 440, 1123.

Wu, T.H., et al. Photothermal nanoblade for large cargo delivery into mammalian cells. Anal. Chem. (2011) 83, 1321-1327.

Yoo, J.W., Irvine, D.J., Discher, D.E. & Mitragotri, S. Bio-inspired, bioengineered and biomimetic drug delivery carriers. Nat Rev Drug Discovery (2011) 10, 521-535.

Zhang, S., Li, J., Lykotrafitis, G, Bao, G. & Suresh, S. Size-Dependent Endocytosis of Nanoparticles. Adv Mater (2009) 21, 419-424.

\* cited by examiner

CATALYTIC DELIVERY NANOSUBSTRATES (CDNS) FOR HIGHLY EFFICIENT DELIVERY OF BIOMOLECULES

This application claims the benefit of the filing date of U.S. Provisional Applications 61/510,263, filed Jul. 21, 2011, which is incorporated by reference herein by reference in its entirety.

The invention was made with Government support under Grant No.CA151159, awarded by the National Institutes of Health. The Government has certain rights in this invention.

BACKGROUND INFORMATION

Cellular machinery is governed by a complicated molecular circuitry consisting of a diverse range of biomolecules that exhibit synergistic functions and interactions. Cell behaviors can therefore be modulated by introducing different biomolecules that specifically perturb crucial effectors in the cellular circuitry[1-3]. Over the past decades, many different approaches have been developed to deliver biomolecules of interest into cells. For example, viruses have been the most commonly used carriers that can dependably deliver genes in vitro[4,5] and in vivo[6,7]. However, viral vectors raise safety concerns due to the risk associated with random insertions of viral DNA into human genome[8-10]. A broad collection of artificial (non-viral) vectors[11-15] has been engineered to overcome viral genomic integration issues. However, the low delivery efficiency compromises their general utility in different cell types. Alternatively, physical delivery techniques[16], such as microinjection,[17] electroporation,[19] continuous infusion[20], sonication[21] and delivery by gene gun[18], were developed to directly introduce biomolecules into cytoplasm. But, the penalty that comes with utilizing physical delivery techniques is mechanical damage that could harm cells' viability and functions. Overall, creating highly efficient universal platform technologies for biomolecular delivery remains one of the major challenges in the field. In addition, these technologies must also meet certain criteria, including (i) general applicability for delivering a diverse range of biomolecules into a wide spectrum of cell types, (ii) minimal disruption to cell viability and functions, and (iii) capability of sequential delivery that sustains a steady supply of biomolecules over the duration of a desired biological process (e.g., direct conversation or reprogramming of somatic cells into different cell lineages).

DESCRIPTION OF THE DRAWINGS

FIG. 1 shows Catalytic Delivery NanoSubstrates (CDNS).

FIG. 2a shows SEM images of the Ad-SiNWS, which were prepared from wet-etching followed by covalent functionalization of Ad. The diameters and lengths of Ad-SiNWS are ca. 100-200 nm and 15-20 μm, respectively. FIG. 2b: upon exposure of 100-nm pEGFP SNPs in the solution/medium to Ad-SiNWS, the resulting pEGFP ⊂ SNPs-grafted Ad-SiNWS were examined by SEM. The narrow size distribution (106±5 nm) of pEGFP ⊂ SNPs on Ad-SiNWS agrees with that observed by DLS measurements (inset). Figures c and d show that free Ad-SiNWS and pEGFP ⊂ SNPs-grafted Ad-SiNWS were released from the substrates, and their morphology and sizes were further examined by TEM.

FIG. 3a shows dose-dependent transfection studies of CDNS platform and three control studies (i.e., Lipo-2000, RGD-jet-PEI and pEGFP ⊂ SNPs in the absence of the Ad-SiNWS), performed in parallel; FIG. 3b shows time-dependent transfection studies in the presence of pEGFP ⊂ SNPs; maximum transfection was achieved 12 h post administration of pEGFP ⊂ SNPs; FIG. 3c shows that U87 cells transfected by the CDNS platform expressed GFP signals an average of 4.3 to 7.2 times stronger than those observed for U87 cells treated by Lipo-2000, RGD-jet-PEI and pEGFP ⊂ SNPs alone; FIG. 3d shows a diversity of mammalian cells, including adherent cells (i.e., Hela, NIH3T3, MCF7 and HEK293), suspension cells (i.e., BC-1, Ramos and Jurkat), and primary cells (i.e., BJ, HDF, J1, MEF and hNSC) which were introduced onto CDNS platform in the presence of pEGFP ⊂ SNPs. CDNS exhibited 70-98% transfection efficiency among different mammalian cells, significantly higher than those observed for a Lipo-2000-based delivery system at similar experimental conditions. FIG. 3e shows a side-by-side comparison of the transfection studies observed for four category of substrates (including Siflat, Ad-Siflat, SiNWS without Ad coating and Ad-SiNWS). As shown in the micrograph images, both Ad recognition motif and SiNWS play important roles in achieving the enhanced transfection performance of CDNS platform. FIG. 3f shows that Ad-SiNWS can be used repeatedly for at least 10 cycles of transfection studies without compromising their transfection performance. FIG. 3g shows a single batch of U87 cells on Ad-SiNWS which were sequentially treated by three different SNP vectors with encapsulated DNA plasmids (specifically encoding EGFP, mCherry and E2-Crimson) at 12, 24 and 36 h post cell settlement. Each individual gene can be effectively delivered into and then expressed by the cells with superb transfection performance.

FIG. 4a shows the suppression of the EGFP expression in a genetically modified U87 cell line (EGFP-U87) in the presence of siRNA ⊂ SNPs (50-ng siRNA/chamber). The EGFP expression of EGFP-U87 cells was silenced to 28±18% and 7±4% at 24 and 48 h post treatment, respectively. FIG. 4b: To examine the GAL4-VP16TF (TF) transduction performance of CDNS platform, cell uptake studies were performed by incubating TF ⊂ SNPs (10-ng TF/chamber) with U87 cells on Ad-SiNWS at variable periods (i.e., 0.5, 1, 2, 4, 6 and 12 h). TF was labeled by Cy5 dye to allow quantitative monitoring of the delivery performance of CDNS platform. The time-dependent uptake studies revealed that accumulation of the fluorescence signals increased with the incubation time and reached saturation at 4 h. FIG. 4c: Fluorescence micrographs showed strong Cy5 signals, confirming the presence of TF in the cell nuclei, where TF functions as a regulator by controlling the translation of specific gene(s); FIG. 4d shows the quantification of the luciferase expression by measuring the bioluminescence intensity of U87 cells treated with TF ⊂ SNPs on Ad-SiNWS and the SNP vector control group for 24 h on a microplate reader and a cooled CCD camera.

FIG. 5 shows direct programming of fibroblast cells into induced neuron-like (iNl) cells using CDNS platform.

DESCRIPTION

Figure 1A:
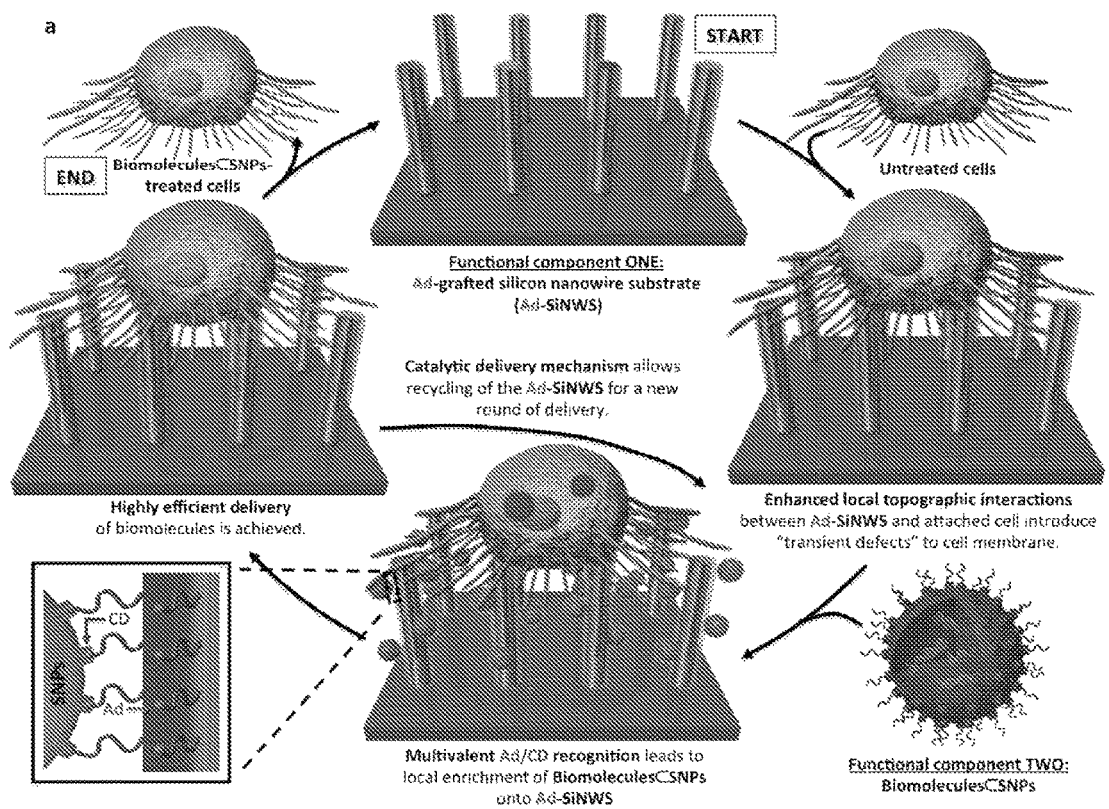
FIG. 1a shows a schematic illustration of the proposed catalytic mechanism that governs the highly efficient biomolecular delivery of CDNS platform. Cells first settle onto an Ad-SiNWS, resulting in "transient defects" in the cell membranes due to enhanced local topographic interactions between cell membranes and Ad-SiNWS. Upon exposure of biomolecules ⊂ SNPs to Ad-SiNWS, multivalent molecular recognition between the Ad motifs on SiNWS and the CD motifs on the biomolecules ⊂ SNPs leads to local enrichment of biomolecules ⊂ SNPs from the surrounding solution/medium onto Ad-SiNWS. Consequently, the enriched biomolecules ⊂ SNPs on Ad-SiNWS dynamically detach and enter the Ad-SiNWS-immobilized cells through the "transient defects", achieving a highly efficient delivery of biomolecules. Such an operation mechanism allows for the repeated use of Ad-SiNWS, as well as the repeated delivery of multiple batches of biomolecules.

This invention relates, e.g., to a new technology (molecular delivery system) for efficiently delivering molecules of interest into any of a wide diversity of cells. This molecular delivery system is sometimes referred to herein as a Catalytic Delivery NanoSubstrate (CDNS).

One element (component) of the delivery system is a substrate having (attached thereto) a nanostructured surface region which comprises a plurality of nanostructures, wherein, covalently attached (bound) to the nanostructured surface region are multiple copies of a first member of a binding pair. This nanostructured surface region is sometimes referred to herein as a "nanostructural substrate" or a "nanosubstrate." The nanostructures increase the surface area of the substrate and increase the probability that a given cell will come into contact with the surface. When cells are contacted with the nanosubstrate, enhanced topographic interactions[12,13] between the nanostructures and nanoscale components of the surface of the cells, such as microvilli and filopedia, result in a high degree of membrane substrate surface area contact. A variety of suitable types of nanosubstrates are discussed elsewhere herein, including the nanowire-comprising device for capturing circulating cells described in a publication by the inventors, international application WO2010/108003, published Sep. 23, 2010.

A second element (component) of the delivery system is one or more vector nanoparticles (sometimes referred to herein as nanoscale vectors), each of which comprises, encapsulated therein, a molecule (e.g. a biomolecule) of interest, which is sometimes referred to herein as a payload or cargo, to be delivered to a cell. Each vector nanoparticle comprises, on its surface, multiple copies of a second member of the binding pair. A variety of suitable types of vector nanoparticles are discussed elsewhere herein, including the supramolecular nanoparticles (SNPs) described in a publication by the inventors, international application WO2010/099466, published Sep. 2, 2010.

One aspect of the invention is a method for delivering a molecule of interest into a cell, comprising contacting the cell with a nanosubstrate as described above so that the cell is associated with (in proximity to) the nanosubstrate, then immobilizing one or more vector nanoparticles as described above, in situ onto the nanosubstrate via interaction between the first and second members of the binding pair. Without wishing to be bound by any particular mechanism, it is suggested that the vector nanoparticles are then dissociated from the nanostructural substrate and delivered into the cells, and that the molecule of interest (the cargo) is released into the cells. As used herein, the singular forms "a," "an" and "the" include plural referents unless the context clearly dictates otherwise. For example, "a" molecule as used above includes one or more molecules, which can be the same or different.

The cells can then be detached for further use, or can interact with additional vector nanoparticles to deliver more of the same cargo, or an additional cargo, for one or multiple times.

One advantage of a molecular delivery system and method of the invention is that molecules are delivered to a cell in a catalytic manner. Without wishing to be bound by any particular mechanism, the following mechanism may account for the results reported herein: The nanosubstrate (with the first member of the binding pair) exhibits enhanced local topographic interactions with cells immobilized on the nanosubstrates, resulting in "transient defects" on the cell membranes. When vector nanoparticles (with the first member of the binding pair and containing biomolecular payloads) are exposed to the nanosubstrate, multivalent molecular recognition between the first member of the binding pair on the nanosubstrate and the second member of the binding pair on the vector nanoparticles leads to dynamic assembly and local enrichment of vector nanoparticles from the surrounding solution/medium onto the nanosubstrate. Subsequently, vector nanoparticles enriched on the nanosubstrate can dynamically detach and diffuse into the nanosubstrate-immobilized cells through the "transient defects" on the cell membranes. After the dynamic dissociation of vector nanoparticles, highly efficient delivery of biomolecular payloads can be achieved without depending on the endocytic mechanism normally observed for cellular uptake of nanoparticles. Such an operation mechanism allows for the repeated use of nanosubstrate for multiple rounds of delivery. Alternatively, delivery of multiple batches of biomolecules can be accomplished by sequential additions of the corresponding vector nanoparticles, thus sustaining a steady supply of biomolecules for long-term cell manipulations. Similar to how a conventional chemical catalyst enhances the efficiency of a given reaction by lowering free energy of activation and can be recycled for multiple rounds of a reaction, the nanosubstrate is capable of facilitating the highly efficient and repeated delivery of vector nanoparticles into the nanosubstrates-immobilized cells.

Another advantage of a molecular delivery system of the invention is that following the delivery of the cargo, additional vector nanoparticles, carrying the same or different cargos, can be immobilized on the nanosubstrates (brought into association with, or in proximity to, the cells) in order to deliver their cargos into the cells. It is not necessary to prepare a new nanosubstrate (e.g. to recoat the nanosubstrate with a biomolecule to be delivered, or to recoat the nanosubstrate with an affinity molecule, such as a member of a binding pair, that will attract a particle comprising a biomolecule to be delivered) in order to deliver additional cargos. This allows for continuous delivery of molecules of interest, or sequential delivery of molecules of interest, such as genes or proteins.

Another advantage is that the vector nanoparticles can encapsulate a wide diversity of molecules (e.g., biomolecules), including, e.g., genes, proteins, drugs, reporters, or combinations thereof; and can transport them into a wide variety of cell types, including cells into which it is difficult to introduce exogenous molecules using traditional methods of transfection of nucleic acids or transduction of peptides or proteins. These cell types include, e.g., primary cells, stem cells, neurons, or immune cells.

Other advantages of the above-described delivery systems and methods are that the methods can be performed in vitro or in vivo, and that exogenous molecules can be delivered into cells with high efficiency, with minimal disruption of cell viability and functions. As a result, unwanted side effects associated with gene transfection or transduction (such as introducing cancerous genes into the genome or activating multiple different subcellular pathways) are greatly decreased. Also, given the high delivery efficiency and the ability to deliver different molecules sequentially, massive parallel screening (e.g. assaying different molecules in the same cell or different cells in a short period of time) can be achieved.

In addition, delivery systems and methods of the invention can be used to deliver molecules of interest to prokaryotic cells. This allows for a variety of applications, including, e.g., large-scale parallel antibiotic screening.

Furthermore, delivery systems of the invention can easily be mass produced, by high-throughput, low-cost methods, allowing for wide-range application of the delivery methods of the invention.

One aspect of the invention is a molecular delivery system comprising:
A. a substrate having
 (i) a nanostructured surface region which comprises a plurality of nanostructures and,
 (ii) covalently attached to the nanostructured surface region, multiple copies of a first member of a binding pair; and B. at least one vector nanoparticle which comprises
 (i) encapsulated therein, a molecule of interest and,
 (ii) on its surface, multiple copies of second member of the binding pair.

Another aspect of the invention is a method for delivering a molecule of interest into a cell, comprising
A. contacting the cell with a substrate having a nanostructured surface region which comprises a plurality of nanostructures, to which are covalently attached multiple copies of a first member of a binding pair, so that the cell is associated with the nanostructured surface region; then
B. immobilizing (contacting) on the nanostructured surface region with which the cell is associated at least one vector nanoparticle, wherein the vector nanoparticle encapsulates the molecule of interest and comprises, on its surface, multiple copies of a second member of the binding pair,
 so that (under conditions such that) the vector nanoparticle is internalized (taken up) by the cell and the molecule of interest is released from the vector nanoparticle and is delivered to the cell.

Another aspect of the invention is a method for delivering repeated doses of a first molecule of interest, or delivering a second (and third, fourth, etc as desired) molecule of interest, into the cell as above. In this method, after a first molecule has been delivered by a method as above, the method further comprises contacting the nanostructured surface region with which the cell is associated with at least one vector nanoparticle comprising multiple copies of the second member of the binding pair, but wherein the vector nanoparticle encapsulates more of the first molecule, or encapsulates a second molecule, so that (under conditions such that) the vector nanoparticle is internalized by the cell and the molecule of interest is released from the vector nanoparticle and is delivered to the cell.

Another aspect of the invention is a kit for delivering a molecule of interest into a cell, comprising in one container a substrate comprising a nanostructured surface region of the invention to which is covalently attached multiple copies of a first member of a binding pair; and in a second container, a (at least one) vector nanoparticle encapsulating the molecule of interest and comprising on its surface multiple copies of a second member of the binding pair.

Any of a variety of substrates and nanostructured surface regions can be used in a delivery system or method of the invention. The term "nanostructure" refers to a structure having a lateral dimension and a longitudinal dimension. In general, the lateral dimension, the longitudinal dimension, or both the lateral and longitudinal dimensions are less than 1 mm. The shape of the nanostructure is not critical. It can be, e.g., any three dimensional surface such as a bead, particle, strand, tube, sphere, etc. The nanostructured surface region can comprise, as nanostructures, nanowires or nanofibers made of an inorganic material (e.g. silicon or metals such as titanium, aluminum, or steel, or an inorganic oxide, such as zinc oxide, silicon oxide, titanium oxide or aluminum oxide). The term nanowire or nanofiber refers to a material in the shape of a wire or rod having a diameter in the range of 1 nm to 1 μm. Such wires or fibers can be oriented substantially perpendicular to, or substantially horizontal to, the substrate. In another embodiment, the nanostructured surface region comprises, as nanostructures, organic polymers, comprising e.g. at least one of polymethyacrylate, polysaccharide, or polylactide. Such polymers can be attached to the substrate so they are oriented substantially perpendicular to, or substantially horizontal to, the surface. See international application WO2010/108003, which is incorporated by reference herein in its entirety, for a discussion of some suitable surfaces and nanostructured surface regions that can be used in a delivery system or method of the present invention.

In one embodiment, the nanostructured surface region comprises silicon nanowires or nanofibers in which the longitudinal dimension is at least ten times greater than the lateral dimension. In embodiments of the invention, the diameter ranges from about 50-500 nm and the length ranges from about 100 nm to as long as about several meters, in the case of electrospun nanofibers. As used herein, the term "about" means plus or minus 5% of the value.

Any of a variety of vector nanoparticles can be used in a delivery system or method of the invention. As used herein, the term "vector nanoparticle" refers to a nanoparticle which can carry a cargo to be delivered to a cell. In general, vector nanoparticles are about 50-500 nm in diameter. Suitable vector nanoparticles, which can encapsulate a molecule of interest to be delivered to a cell, and which can comprise, on their surface, multiple copies of a member of a binding pair, will be evident to a skilled worker. For example, the vector nanoparticles can be liposomes, self-assembled nanoparticles based on amphiphilic polymer, inorganic nanoparticles (e.g., Au, Ag, $TiO_2$, or iron oxide nanoparticles), polymer-based nanoparticles (e.g., polymer-drug and DNA/polymer complexes) or sol-gel nanoparticles ($SiO_2$ nanoparticles).

In one embodiment of the invention, the nanoparticles are the supramolecular nanoparticles (SNPs) described in WO 2010/099466, which is incorporated by reference herein in its entirety. In the representative molecular delivery system and method of using it shown in the present Examples, adamantane-grafted silicon nanowire substrates (Ad-SiNWS) are used. These are shown to introduce "transient defects" into cell membranes of AdSiNWS-immobilized cells, allowing dynamically enriched biomolecules ⊂SNPs to diffuse into the cells.

Briefly, SNPs comprise three structural elements: (1) a plurality of structural components that are suitable to at least provide some mechanical structure to said supramolecular structure; (2) a plurality of binding components, each having a plurality of binding regions adapted to bind to said plurality of structural components; and (3) a plurality of terminating components, each of which is adapted to bind to a binding region of one of said plurality of binding components. The plurality of structural components and the plurality of binding components self-assemble when brought into contact to form the supramolecular structure, and the plurality of terminating components act to occupy binding regions of said plurality of binding components to terminate further binding when the plurality of terminating components are present in a sufficient quantity relative to said plurality of binding regions of said plurality of binding components.

In one embodiment of the SNPs, the plurality of structural components comprise a plurality of binding elements that bind to the binding regions. In one embodiment, the binding regions bind to the terminating components or structural components to form a molecular recognition pair, such as the inclusion complex diazobenzene-α-cyclodextrin or, preferably, adamantane-β-cyclodextrin. It is the latter embodiment of SNPs which is shown in the Examples herein.

In an SNP of the present invention, each SNP comprises (encapsulates) a biomolecule of interest to be delivered; and at least one of the structural component, binding component or terminating component further comprises a second member of the binding pair.

In some embodiments, a vector nanoparticle further comprises a functional element. The functional element can be bound to any portion of the nanoparticle. For example, in the case of an SNP, the functional element can be bound to or otherwise associated with a structural component, a binding component or a terminating component. A functional element is a chemical moiety that imparts an additional function or activity to the vector nanoparticle that is not present when the functional element is missing. In some embodiments, the functional element is a light emitting (i.e. fluorescent or phosphorescent) compound. Fluorescent and phosphorescent labeled supramolecular structures may be used, for example in imaging studies in vitro or in vivo. In other embodiments, the functional element may be a compound having a radioactive or magnetically active isotope. For example, positron emitting isotopes, such as $^{64}Cu$ may be used to measure biodistribution of the vector nanoparticles. Other suitable isotopes will be readily apparent to one of ordinary skill.

In some embodiments, the functional element is a cell permeation element, which functions to increase cell membrane permeation. Specific examples of ligands that increase cell membrane permeation include the TAT ligand. Other cell membrane permeation ligands may also be used.

Any of a variety of binding pairs can be used to facilitate (enhance, aid in) the immobilization (association or interaction) of vector nanoparticles on nanostructured surface regions. Binding pairs which exhibit a strong enough binding affinity will be evident to a skilled worker. The interactions can include, e.g., noncovalent bonding such as hydrogen bonding, metal coordination, biomolecular interactions, hydrogen bonding interactions, dipole-dipole interactions, hydrophobic forces, van der Waals forces, π-π interactions, halogen bonding, electrostatic and/or electromagnetic effects.

In general, one member of a binding pair is covalently bound to the nanostructured surface region and the other member is covalently attached to the vector nanoparticle. In general, it is important that both attachments be covalent. Non-covalent bonds would likely result in the binding members coming on and off the structures dynamically, lessening the advantages of their specific recognition, e.g. for self-assembly and subsequent catalytic delivery. Multiple copies of the binding pair members are present on both the nanostructured surface region and the vector nanoparticles. The members of the binding pair may coat the nanostructured surface and/or vector nanoparticle completely or partially. Methods of attaching the binding agents (e.g., methods of bioconjugation) are conventional and well-known to those of skill in the art. For each of the members of the binding pairs suggested herein, either one can be on the surface and the other on the vector nanoparticle.

Suitable binding pairs include inclusion complexes, e.g. of adamantane-β-cyclodextrin or diazobenzene-α-cyclodextrin. In one embodiment, the vector nanoparticles are SNPs in which the structural components are adamantane and cyclodextrin, as described in WO2012/099466. In this embodiment, the first member of the binding pair can be adamantane (from the particle) and the second member of the binding pair, which is present on the nanostructured surface, β-cyclodextrin; or the first member (from the particle) can be β-cyclodextrin, and the second member (present on the nanostructured surface, adamantane. See the Examples herein for a representative delivery system, in which SNPs comprising adamantane and cyclodextrin, and nanostructured surfaces comprising nanowires coated with adamantane, are used. In other embodiments, components of the SNPs can be functionalized with other members of binding pairs, which react with their counterparts attached to the nanostructured surfaces.

Other suitable binding pairs include biotin/streptavidin, a variety of ligands and their receptors, and combinations of antigen-antibody, protein-inhibitor, protein-protein; or a pair of complementary oligonucleotides (e.g., DNA-DNA, DNA-RNA, RNA-RNA, or modified nucleic acids such as PNA or LNA). Other suitable binding pairs based on specific interaction between two molecules through noncovalent bonding such as hydrogen bonding, metal coordination, hydrophobic forces, van der Waals forces, π-π interactions, halogen bonding, electrostatic and/or electromagnetic effects (e.g., adamantane and cyclodextrin) will be evident to a skilled worker.

Any of a variety of molecules (e.g., biomolecules or other chemical entities) can be encapsulated in vector nanoparticles, as cargo or a payload, for delivery to a cell. Such molecules include, e.g., therapeutic agents, markers, reporters, or imaging agents. The cargo can be a nucleic acid (e.g. plasmids comprising nucleic acids which encode proteins for use in gene therapy, oligonucleotides, siRNAs, antisense molecules, etc), a protein (e.g. an antibody, protein or peptide), a polysaccharide, or a small molecule (e.g. therapeutic compounds such as doxorubicin, taxol, rapamycin or cis-platin for cancer therapy). In some embodiments, a vector nanoparticle encapsulates two or more therapeutic cargo compounds, e.g. allowing for delivery of a defined ratio of therapeutic compounds to a cell by adjusting the ratio of the therapeutic compounds. Other combinations may be used. Many other types of cargo will be evident to a skilled worker. The vector nanoparticles may protect cargo, such as therapeutic compounds, proteins or oligonucleotides, from degradation prior to delivery.

Methods of making and assembling the components of molecular delivery systems of the invention are conventional and well-known to those of skill in the art. Some such methods are described in the publications described herein.

A method of the invention may be employed to deliver a molecule of interest to any of a variety of types of cells. These include prokaryotic (e.g. bacterial) cells and eukaryotic cells (such as, e.g., yeast, *Drosophila* and other insect cells, and mammalian cells, including cells from pets, farm animals, experimental animals, non-human primates and humans). The cells can be, e.g., cells that can be grown in culture (see, e.g., the Examples), stem cells, neurons, immune cells (e.g. dendritic cells), somatic cells (e.g. fibroblasts), or primary cells. Plant cells can also be used.

In a method of the invention, the cells are contacted with the nanostructured surface region, so that the cell becomes associated with the nanostructured surface region When cells are capable of adhering to a surface, they can be plated onto the surface in a suitable medium and, optionally, can be incubated, cultured, grown etc. so that they adhere to the nanostructured surface. These types of cells are "associated" with the nanostructured surface region in that they are attached or bound to the surface. Other types of cells, such as immune cells, which do not adhere to surfaces, are "associated" with the nanostructured surface region in that they are in proximity to the surface region, albeit it sometimes transiently. In either case, the cells are in close enough proximity to the binding pair members which are covalently bound to nanostructured surface region so that, when a vector nanoparticle is immobilized on the surface via a binding pair interaction, the vector nanoparticle will be close enough to the cell to be internalized by the cell.

Subsequent to contacting the cells with the nanostructured surface region, at least one vector nanoparticle encapsulating a molecule of interest to be delivered to the cells is then immobilized on the nanostructured surface region containing the cells. The vector nanoparticle becomes immobilized in situ onto the nanosubstrate via interaction between the first and second members of the binding pair (the first binding pair member on the nanosubstrate and the second binding pair member on the nanoparticle). In general, the vector nanoparticles can be added to the surfaces almost immediately after the cells have been added, although the cells may be cultured for a period of time before the vector nanoparticles are added.

Without wishing to be bound by any particular mechanism, it is suggested that because of the proximity of a cell to an immobilized vector nanoparticle, the vector nanoparticle contacts and is taken up by (internalized by) the cell. It is noted that the molecules to be delivered are not directly coated onto the nanosubstrate (e.g., coated onto nanowires, or attached to them by a linker) but rather are encapsulated by vector nanoparticles which are immobilized on the nanosubstrate. The vector nanoparticles are then dissociated from the nanostructural substrate, delivered into the cells, and the cargo molecules of interest (the cargo) are released into the cells.

Conditions effective for the uptake of vector nanoparticles into a cell and release of the cargo into the cell include suitable temperatures and other conditions that will be evident to a skilled worker. As noted above, it is generally not necessary to incubate or culture the cells before the vector particles are added.

A delivery system of method of the invention can be used for many applications.

For example, experiments may be conducted in which cells are transfected with a nucleic acid or transduced with a protein, either in vitro or in vivo, in order to evaluate the effect of the substance on properties of the cell. For example, concentration-dependent effects of a particular protein, RNA, drug, and/or combinations thereof can be studied. Alternatively, by perturbing different elements of a particular cellular pathway, the causal relationships between those elements can be elucidated.

In another embodiment, differentiated cells are reprogrammed into induced pluripotent stem cells by delivering suitable proteins, RNAs or small molecules to the cells, in vitro or in vivo. Similarly, the delivery systems can be used to study the effects of numerous molecules on differentiating or altering the development of any set of cells, such as stem cells, induced pluripotent stem cells, and already differentiated tissues. Once the chemicals to develop a particular cell lineage are discovered, the delivery system can be used to generate that line.

In another embodiment, cells that are removed from a subject or obtained elsewhere can be transfected with a suitable nucleic acid or transduced with a suitable protein by a method of the invention, then transplanted back into the subject in methods of ex vivo treatment. For example, cardiac tissue can be treated to introduce a substance such as VEGF and then reimplanted into a damaged heart in order to treat heart disease.

In another embodiment, cells are transfected or transduced in vivo (in a subject).

Other uses for the delivery systems and methods of the invention will be evident to a skilled worker.

When substrates having a nanostructured surface region as described herein are administered to a subject, or when vector nanoparticles are administered to a subject, they are generally formulated as pharmaceutical compositions. A "pharmaceutical composition" comprises a component of a molecular delivery system of the invention plus a pharmaceutically acceptable carrier or diluent. In some embodiments, the component of the molecular delivery system is present in an effective amount for the desired purpose. "Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The components of molecular delivery systems of the invention can be formulated as pharmaceutical compositions in a variety of forms adapted to the chosen route of administration, for example, orally, nasally, intraperitoneally, or parenterally, by intravenous, intramuscular, topical or subcutaneous routes, or by injection into tissue. Methods for making and using such formulations are conventional and well-known in the art.

Another aspect of the invention is a kit for delivering a molecule of interest into a cell, comprising in one container a substrate comprising a nanostructured surface region of the invention to which is covalently attached multiple copies of a first member of a binding pair; and in a second container, at least one vector nanoparticle encapsulating the molecule of interest and comprising on its surface multiple copies of a second member of the binding pair. A kit of the invention may comprise instructions for performing a method of the invention. Other optional elements of a kit of the invention include suitable buffers, media components, or the like; additional containers; or packaging materials. Reagents for performing suitable controls may also be included, e.g. if the efficacy of a drug or drug candidate is being evaluated. A skilled worker will recognize components of kits suitable for carrying out any of the methods of the invention.

The following Examples illustrate, as proof of principle, one embodiment of the invention. Other types of molecular delivery systems, and other methods of delivery, are of course encompassed by the invention.

In the foregoing and in the following examples, all temperatures are set forth in uncorrected degrees Celsius; and unless otherwise indicated, all parts and percentages are by weight.

EXAMPLES

Example I—Catalytic Delivery of Nanosubstrates for Introducing Functional Biomolecules That are Encapsulated in Supramolecular Nanoparticles A. Methods Preparation of Adamantane-Grafted Silicon Nanowire Substrates (Ad-SiNWS).

We fabricated SiNWS via a wet chemical etching process[40]. First, the surface of the silicon substrate was made hydrophilic according to the following procedure: The silicon wafer was ultrasonicated in acetone and ethanol at room temperature for 10 and 5 min, respectively, to remove contamination from organic grease. Then, the degreased silicon substrate was heated in boiling Piranha solution (4:1 (v/v) $H_2SO_4/H_2O_2$) and RCA solution (1:1:5 (v/v/v) $NH_3/H_2O_2/H_2O$) each for 1 h. Subsequently, the silicon substrate was rinsed several times with deionized water. Then, the clean silicon substrate was used in a wet chemical etching process. An etching mixture consisting of deionized water, 4.6 M HF, and 0.2 M silver nitrate was used at room temperature. The etching duration was dependent upon the required length of the nanowires. After etching, the substrate was immersed in boiling aqua regia (3:1 (v/v) $HCl/HNO_3$) for 15 min to remove the silver film. Finally, the substrate was rinsed with DI water, dried under nitrogen and ready for surface modification. The surface modifications of the SiNWS and Siflat were processed with 4% (v/v) 3-aminepropyl trimethoxysilane in ethanol at room temperature for 45 min. Then, the Siflat and SiNWS were treated with the 1-adamantane isocyanate (1.0 mM) in DMSO for 30 min. The modified Siflat and SiNWS were then washed with DMSO twice to remove excess 1-adamantane isocyanate. The substrates were rinsed with DI water three times and stored at 4-8° C.

General Procedure for Treatment of Cells with Biomolecules ⊂ SNPs Using CDNS.

Figure 3:
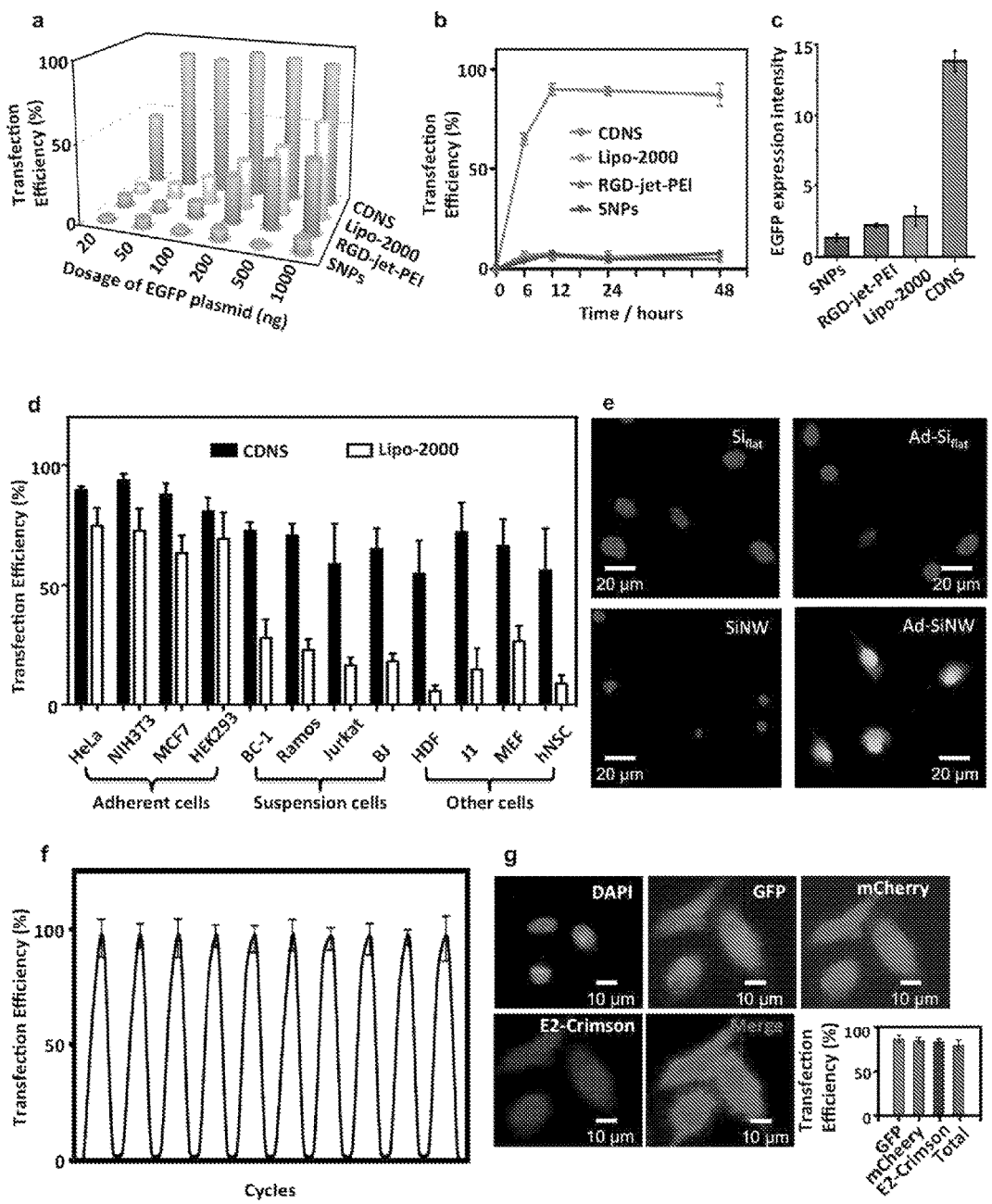
FIG. 3 shows highly efficient delivery of genes using CDNS platform.
Figure 4:
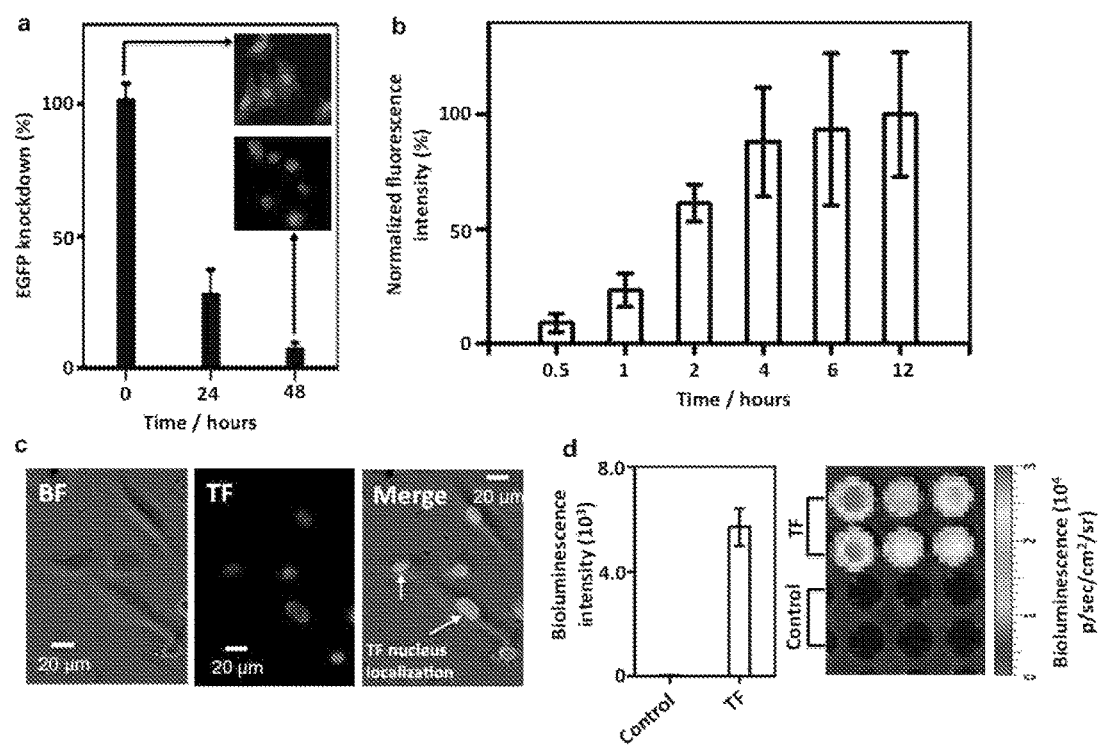
FIG. 4 lshows the general applicability of CDNS platform for delivery of siRNA and a transcription factor.

$5 \times 10^4$ candidate cells were introduced into each well of a 2-well chamber slide (Lab-Tek®), in which a 1×2 $cm^2$ Ad-SiNWS was placed in the bottom of the chamber. After the cells fully attached onto Ad-SiNWS (for 12 h), the chambers were washed with PBS and refilled with fresh cell culture medium. Then, different quantities of 100 nm biomolecules ⊂ SNPs (containing 20 ng to 1 μg of biomolecules) were introduced into individual chambers and co-incubated with attached cells for 24 h. After the chamber was washed with PBS, the cells were immediately fixed with 2% PFA and stained with DAPI. Transfection performances of individual conditions were quantified using microscopy-based image cytometry and summarized in FIG. 3 and FIG. 4.

Generation of iNl Cells and Immunofluorescence Staining.

Approximately $1.0 \times 10^5$ mouse embryonic fibroblast (MEF) passage 4, human dermal fibroblast (HDF) cells passage 8 or human foreskin fibroblast passage 8 were first plated into each well of a 2-well chamber slide containing an Ad-SiNWS and DMEM cell culture medium. 100-nm pNTFs ⊂ SNPs were prepared by incorporating a mixture of four different NTF plasmids (i.e., Ascl1, Brn2, Mytl1 and NeuroD1[37,38]) into the SNP vector. After 24-h settlement of the cells, the DMEM cell culture medium was first replaced by a neuronal cell culture medium. NTFs expression was induced in Tet-On by doxycycline (1 μg/mL) treatment. Subsequently, 100-nm pNTFs ⊂ SNPs (125-ng plasmid/chamber for each NTF) were introduced into the individual chambers every 24 h for the first 4 d and every 48 h for the following 6 d in order to sustain steady supply of the four NTFs over the conversion process. After 11 or 15 d of fibroblast-iNl cell conversion, the resulting iNl cells on the Ad-SiNWS were washed with PBS three times and then fixed in 4% paraformaldehyde solution for 10 min at room temperature. Prior to immunochemical staining, the fixed iNl cells were incubated for 30 min in TNBS (PBS supplemented with 0.4% Triton-X 100 and 5% goat serum) to improve their permeability. Cells were then incubated at 4° C. overnight in TNBS containing the primary antibodies, Tuj1 (Covance, 1:500), Map2 (Sigma, 1:200), NeuN (Millipore, 1:200), and Nestin (Santa Cruz, 1:200). After washing with TNBS, cells were incubated in PBS containing the secondary antibodies: Goat anti-mouse Cy3 and Goat anti-rabbit Cy2 (Jackson ImmunoResearch, 1:500) and then stained with Hoechst (5 μg/mL). The stained iNl cells were subjected to fluorescence imaging.

B. Results

This Example describes a new platform technology, pioneering a concept entitled "Catalytic Delivery NanoSubstrate (CDNS, FIG. 1a)" for highly efficient delivery of various biomolecules into a wide spectrum of mammalian cells. Our CDNS technology centers around the use of two functional components with nanoscale features, including (i) an adamantane-grafted silicon nanowire substrate (Ad-SiNWS) obtained by covalently grafting a binding pair member (a molecular recognition motif such as, e.g., adamantane, Ad) onto a densely packed silicon nanowire substrate[22,23] (SiNWS), and (ii) biomolecule-encapsulated supramolecular nanoparticles[24-30] (biomolecules ⊂ SNPs) prepared from self assembly of the molecular building blocks and a wide spectrum of biomolecular payloads. Without wishing to be bound by any particular mechanism, the following mechanism is suggested. Ad-SiNWS exhibits enhanced local topographic interactions[22,31,32] with cells immobilized on Ad-SiNWS, resulting in "transient defects" on the cell membranes. When biomolecules ⊂ SNPs are exposed to Ad-SiNWS, multivalent molecular recognition between the Ad motifs on Ad-SiNWS and the β-cyclodextrin (CD) motifs (inset in FIG. 1a) on the surfaces of biomolecules ⊂ SNPs leads to dynamic assembly and local enrichment of biomolecules ⊂ SNPs from the surrounding solution/medium onto Ad-SiNWS. Subsequently, biomolecules ⊂ SNPs enriched on Ad-SiNWS can dynamically detach and diffuse into the Ad-SiNWS-immobilized cells through the "transient defects" on the cell membranes. After the dynamic dissociation of biomolecules ⊂ SNPs, highly efficient delivery of biomolecules can be achieved without depending on the endocytic mechanism normally observed for cellular uptake of nanoparticles[33,34]. This operation mechanism allows for the repeated use of Ad-SiNWS for multiple rounds of delivery. Alternatively, delivery of multiple batches of biomolecules can be accomplished by sequential additions of the corresponding biomolecules ⊂ SNPs, thus sustaining a steady supply of biomolecules for long-term cell manipulations. Similar to how a conventional chemical catalyst enhances the efficiency of a given reaction by lowering free energy of activation and can be recycled for multiple rounds of a reaction, Ad-SiNWS is capable of facilitating the highly efficient and repeated delivery of biomolecules ⊂ SNPs into the Ad-SiNWS-immobilized cells. Recently, low-density silicon nanowire (SiNW) substrates[35,36] have been employed to penetrate cell membranes, enabling direct delivery of biomolecules already pre-deposited on the SiNW surfaces. In contrast, our CDNS platform is governed by a different mechanism. First, the individual Ad-SiNWS embedded in CDNS platform are not required to penetrate the cell membranes. Consequently, there is negligible disruption to the viability and functions of the Ad-SiNWS-immobilized cells. Second, CDNS platform enables the sequential delivery of biomolecules in SNP vectors using the same substrates without depositing biomolecules and immobilizing cells in each round of delivery.

Figure 1B:
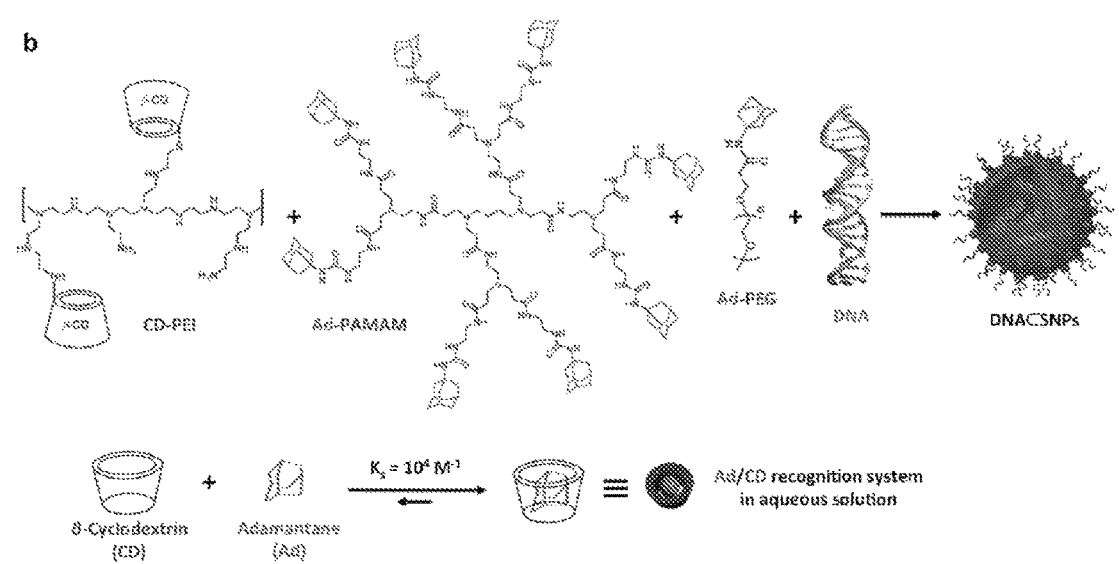
FIG. 1b shows the supramolecular assembly of biomolecules ⊂ SNPs from the three molecular building blocks (i.e., CD-PEI: CD-grafted branched polyethylenimine, Ad-PAMAM: Ad-grafted polyamidoamine dendrimer, Ad-PEG: Ad-grafted polyethylene glycol) and biomolecular payloads (e.g., DNA plasmids, siRNA, or transcription factors).
Figure 2:
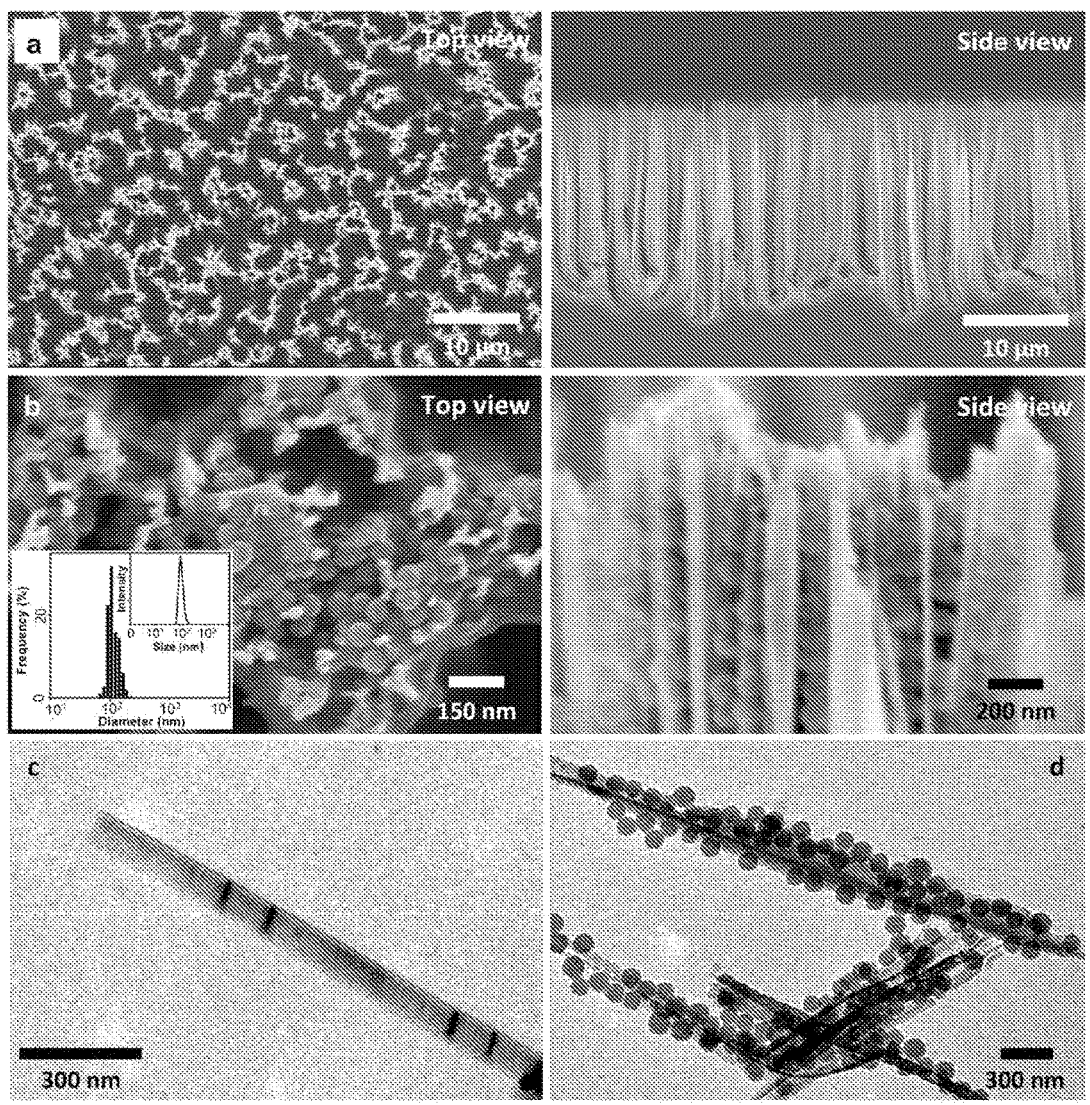
FIG. 2 shows electron microscopy characterization of the morphologies and structures of CDNS.

With regard to our molecular design, three categories of biomolecules ⊂ SNPs have been prepared from common molecular building blocks[30] (i.e., CD-PEI, Ad-PAMAM and Ad-PEG) and respective biomolecule payloads, including DNA plasmid[28,29], siRNA and proteins (transcription factors, TFs)[25]. Here, we pick DNA-encapsulated SNPs (DNA ⊂ SNPs, FIG. 1b) as an example to illustrate the working mechanism of the supramolecular synthetic strategy[24-30]. CD-PEI and Ad-PAMAM first self-assemble, using the complementary recognition motifs (i.e., CD and Ad), into cationic hydrogel networks that can encapsulate[28,29] DNA plasmid, creating the cores of SNPs. The ligand module (Ad-PEG) then acts as a capping/solvation reagent that constrains continuous growth of the DNA-encapsulated hydrogel networks[29], and simultaneously confers desired solubility and structural stability to the resulting DNA ⊂ SNPs with controllable sizes of ca. 100 nm. Again, upon exposure of DNA ⊂ SNPs to Ad-SiNWS, the multivalent Ad/CD molecular recognition (inset in FIG. 1a) induces local enrichment of DNA ⊂ SNPs onto Ad-SiNWS via dynamic exchange[28,29]. (Detail preparations of Ad-SiNWS and DNA ⊂ SNPs-grafted Ad-SiNWS are summarized in Example IA (Methods) above). The molecular mechanism that drives the local enrichment of DNA ⊂ SNPs from the solutions onto Ad-SiNWS is verified by scanning electron microscopy (SEM) images of Ad-SiNWS (FIG. 2a) and EGFP plasmid-encapsulated SNPs28,29 (pEGFP ⊂ SNPs)-grafted Ad-SiNWS (FIG. 2b). The narrow size distribution (106±5 nm) of the immobilized pEGFP ⊂ SNPs (characterized by SEM) agrees with that observed by dynamic light scattering (DLS, inset in FIG. 2b) measurements. Further, free Ad-SiNWs and pEGFP ⊂ SNPs-grafted Ad-SiNWs were released from the silicon substrates via sonication for transmission electron microscopy (TEM FIGS. 2c and d) studies, and their morphology and sizes are consistent with those observed by SEM.

To examine the performance of CDNS platform for gene delivery, dose-dependent transfection studies were first conducted on Ad-SiNWS in the presence of pEGFP ⊂ SNPs[28,29] (20-1000 ng plasmid in 1.0-mL DMEM medium/chamber). 1×2 cm$^2$ Ad-SiNWS were placed in 2-well chamber slides (Lab-Tek®), where 5×10$^4$ U87 glioblastoma cells were introduced into each chamber. Three control studies were performed in parallel, two of which used commercially available transfection agents (i.e., Lipo-2000 and RGD-jet-PEI), and the third contained pEGFP ⊂ SNPs in the absence of Ad-SiNWS. The results (FIG. 3a) indicated that CDNS platform exhibited superb transfection performance (up to 95% transfection efficiency) even at a low dosage of EGFP plasmid (e.g., 50 ng/chamber), significantly outperforming the two commercial agents. After the dose-dependent transfection studies, MTT assays were conducted (Example II), suggesting that CDNS-based gene delivery exhibited negligible disruption to cell viability. Subsequently, we conducted time-dependent transfection studies using pEGFP ⊂ SNPs (50 ng plasmid/chamber), resulting in an optimal transfection efficiency (FIG. 3b, >10-time improvement than the controls) that was achieved 12 h post administration of pEGFP ⊂ SNPs. It is noteworthy that the U87 cells transfected by the CDNS platform expressed GFP signals an average of 4.3 to 7.2 times stronger (FIG. 3c) than those observed for U87 cells treated by Lipo-2000, RGD-jet-PEI and pEGFP ⊂ SNPs alone. To test the general applicability of the CDNS platform, an array of mammalian cells (FIG. 3d) were introduced onto CDNS platform in the presence of pEGFP ⊂ SNPs (50-ng plasmid/chamber). In general, CDNS platform exhibited 70-98% transfection efficiencies among these mammalian cells, significantly higher than those observed for a Lipo-2000-based delivery system. To examine how individual features of Ad-SiNWS contribute to the transfection performance of CDNS platform, three control studies were conducted using flat Si chips (Siflat), Ad-coated Si (Ad-Siflat) chips, and SiNWS without Ad coating; these experiments were then examined with Ad-SiNWS in the presence of pEGFP ⊂ SNPs. The microscopy images of U87 cells shown in FIG. 3e suggest that both Ad recognition motif and SiNWS play important roles in achieving the enhanced transfection performance, supporting our hypothesized CDNS mechanism (FIG. 1, see time-dependent transduction studies in FIG. 7 in Example II). Using SEM, we were able to observe the formation of "transient defects" on the membranes of Ad-SiNWS-immobilized cells, and at the same time visualize the presence of many pEGFP ⊂ SNPs in cytoplasmid nearby the membrane defects (see FIG. 8 in Example II), further validating the hypothesized CDNS mechanism (FIG. 1). Such a mechanism can in principle enable the repeated use of Ad-SiNWS for multiple rounds of delivery. To explore the feasibility of recycling Ad-SiNWS for multiple rounds of delivery, we repeatedly used the same Ad-SiNWS in more than 10 cycles of transfection studies without observing compromised delivery performance (FIG. 3f). Finally, we examined sequential delivery of three different plasmids using the same Ad-SiNWS into the same batch of cells. Three different DNA ⊂ SNPs (specifically encoding EGFP, mCherry and E2-Crimson) were stepwise introduced into U87 cells at 12, 24 and 36 h post cell settlement onto Ad-SiNWS. As shown in FIG. 3g, individual genes can be effectively delivered into and then expressed by the target cells without compromising sequential transfection performances.

To test the general applicability of CDNS platform for the delivery of other biomolecules (i.e., siRNA, and TF), we prepared siRNA ⊂ SNPs[28,29] and TF ⊂ SNPs[25] for delivery studies in conjunction with the use of Ad-SiNWS. A genetically modified EGFP-expressing U87 cell line (EGFP-U87) was employed in the EGFP silencing study using siRNA ⊂ SNPs[28,29]. In the presence of siRNA ⊂ SNPs, the EGFP silencing efficiencies of Ad-SiNWS-immobilized EGFP-U87 cells were quantified by image cytometry technique, revealing that the EGFP expression was suppressed to 28±18% and 7±4% (FIG. 4a) of the original expression level at 24 and 48 h post treatment, respectively. With regard to TF delivery, a mammalian orthogonal fusion TF, GAL4-VP16, was chosen to serve as a model TF. Meanwhile, a plasmid (i.e., pG5E4T-Fluc) containing five tandem copies of GAL4-VP16 matching recognition sequences and a conjugated luciferase reporter was designed for co-encapsulation[25] into the SNP vectors. In the presence of TF ⊂ SNPs, the TF transduction performance of Ad-SiNWS-immobilized U87 cells was examined. Initially, Cy5-labeled GAL4-VP16 was employed to allow quantitative monitoring of TF transduction performance. The time-dependent uptake studies (FIG. 4b) revealed that accumulation of the fluorescence signals increased with the incubation time and approached to saturation at 4 h. Further, high magnification fluorescence micrographs (FIG. 4c) indicated that TF was accumulated in the cell nuclei, where TF functioned as a regulator by controlling the translation of specific gene(s). Subsequently, we were able to quantify the luciferase expression of U87 cells, which reflected the activities of the uptaken TF. The bioluminescence intensities of cell lysates were recorded at 24 h post treatment by both a plate reader and a CCD camera (FIG. 4d). Strong bioluminescence signals were observed for the U87 cells treated with TF ⊂ SNPs after CDNS delivery, suggesting that the TF still remains active to trigger the luciferase expression.

Figures 5A, 5B:
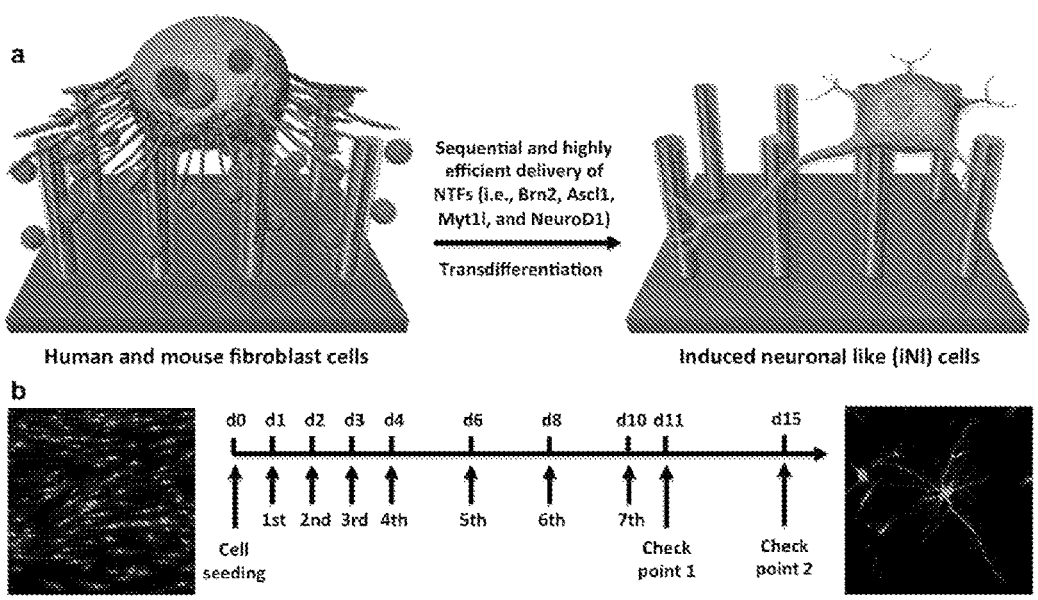
FIG. 5a is a graphic illustration depicting the transdifferentiation of mouse and human fibroblast cells into iNl cells on Ad-SiNWS in the presence of pNTFs ⊂ SNPs containing the four pNTFs (i.e., Ascl1, Brn2, Myt11, and NeuroD1).
FIG. 5b shows a designated timeline which summarizes the 7 sequential treatments of pNTFs ⊂ SNPs, sustaining a steady supply of four NTFs over the transdifferentiation process of 11-15 d.
Figures 5C, 5D:
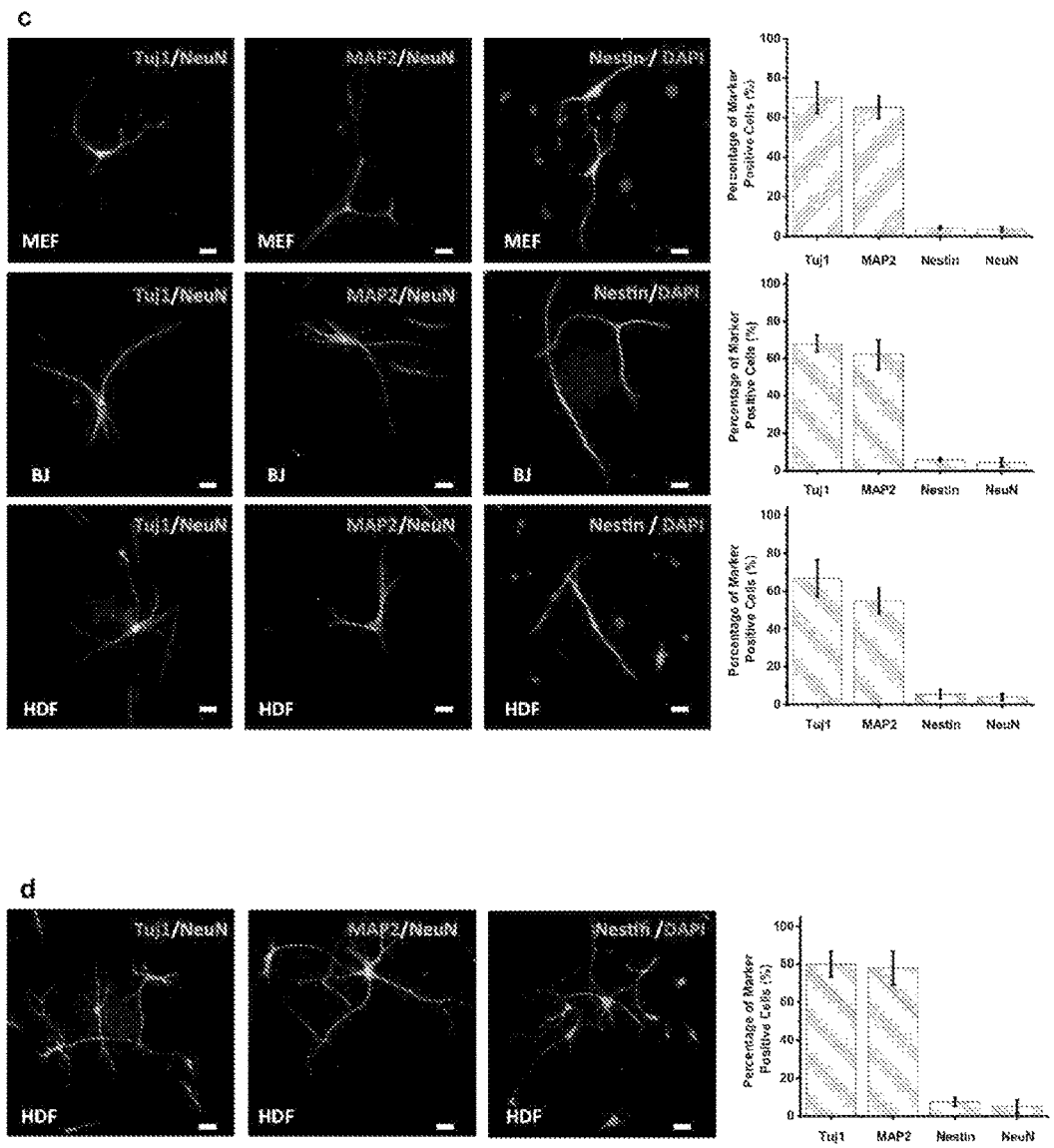
FIG. 5c: At day 11 of the transdifferentiation process, the resulting iNl cells on Ad-SiNWS were immunostained for four neural-cell lineage markers (i.e., Tuj1, Map2, Nestin, and NeuN, scale bars: 20 μm). The percentages of corresponding specific marker-positive cells are also presented to show the conversion efficiency.
FIG. 5d: At day 11, iNl cells were released from Ad-SiNWS and plated on PO/FN treated plates for an additional 4 d. The re-plated iNl cells exhibited a typical neuronal morphology and expressed stable neuronal markers.

Recently, researchers have demonstrated that fibroblast cells can be converted or reprogrammed into induced neuronal like (iNl) cells via viral transfection, which introduces four neuron-specific transcription factors (NTFs including Ascl1, Brn2, Mytl1 and NeuroD1[37,38]). However, the risk associated with viral gene integration[8-10] limits the broad utility of the resulting iNl cells for cell-based therapy. Given the superb performance of CDNS platform demonstrated above, we exploited its potential as an artificial gene transfection system to deliver the four NTFs into fibroblast cells. We show here that we were able to convert these fibroblast cells into the respective iNl cells (FIG. 5a) without encountering the viral gene integration issue. The experimental design and timeline for fibroblast-iNl cell conversion are illustrated in FIG. 5b. pNTFs-encapsulated SNPs (pNTFs ⊂ SNPs) with sizes of ca. 100 nm were prepared by incorporating a mixture of four different NTF plasmids (i.e., Ascl1, Brn2, Mytl1 and NeuroD1[37,38]) into the SNP vector. After seeding mouse or human fibroblast cells on Ad-SiNWS in chamber slides for 24 h, pNTFs ⊂ SNPs (125-ng plasmid/chamber for each NTF) were added to individual chambers every 24 h for the first 4 d and every 48 h for the following 6 d in order to sustain steady supply of the four NTFs over the conversion process. The process of cell fate conversion was assessed by immunofluorescence staining for four neural-stem cells (Nestin) or neuron-specific proteins (i.e., Tuj1, Map2, and NeuN) on both day 11 and day 15 (see time dependent expression for neuron-specific protein of iNl cell in Fig. S4 in Example II). We observed that ca. 50-60% of Ad-SiNWS-immobilized cells expressed the neuron-specific markers, Tuj1 and Map2. Among Tuj1 and Map2-positive cells, about 10% of the cell population expressed neural stem cell marker, Nestin, and mature neuron markers, NeuN. We note that the efficiency observed by CDNS-based fibroblast-iNl cell conversion is comparable with that achieved by lentiviral-based delivery[38]. In order to evaluate whether the iNl cells could maintain the neuronal identity without additional pNTFs ⊂ SNPs, at day 11, the resulting iNl cells were released from Ad-SiNWS and plated on PO/FN (poly-L-ornithine/fibronectin) treated plates for an additional 4 d. Similar to the iNl cells shown on substrates until day 15, the re-plated iNl cells exhibited a typical neuronal morphology and expressed stable neuronal markers (FIG. 5d). Taken together, these results indicated that the CDNS platform can effectively deliver NTFs and promote fibroblast to iNl cells.

To summarize, we have developed "Catalytic Delivery NanoSubstrates" (CDNS) platform capable of introducing various biomolecules (e.g., gene, siRNA and transcription factor) into an array of mammalian cells with profound performance, including high transduction efficiency, minimal disruption to cell viability and functions, and capability of sequential delivery that sustains a steady supply of biomolecules. We explored the use of CDNS platform as an artificial gene transfection system to deliver the four NTFs into fibroblast cells. We were able to convert these fibroblast cells into the respective iNl cells without the need for virus or integrations. Using similar procedures, we expect to apply methods of the invention, including the CDNS platform exemplified herein, to generate other cell lineages and induced pluripotent stem cells, both in vitro and in vivo. We expect that molecular delivery systems and methods of the present invention will provide a superior system for many applications in regenerative medicine including lineage differentiation as well as reprogramming.

REFERENCES

1. Chen, C. S., Mrksich, M., Huang, S., Whitesides, G. M. & Ingber, D. E. Geometric control of cell life and death. *Science* 276, 1425-1428 (1997).
2. Plath, K. & Lowry, W. E. Progress in understanding reprogramming to the induced pluripotent state. *Nat. Rev. Genet.* 12, 253-265 (2011).
3. Izpisua Belmonte, J. C., Ellis, J., Hochedlinger, K. & Yamanaka, S. Induced pluripotent stem cells and reprogramming: seeing the science through the hype. *Nat rev. Genetics* 10, 878-883 (2009).

4. Okita, K., Ichisaka, T. & Yamanaka, S. Generation of germline-competent induced pluripotent stem cells. *Nature* 448, 313-317 (2007).
5. Jaenisch, R., et al. In vitro reprogramming of fibroblasts into a pluripotent ES-cell-like state. *Nature* 448, 318-U312 (2007).
6. Cartier, N., et al. Hematopoietic stem cell gene therapy with a lentiviral vector in X-linked adrenoleukodystrophy. *Science* 326, 818-823 (2009).
7. Kay, M. A., et al. In vivo gene therapy of hemophilia B: sustained partial correction in factor IX-deficient dogs. *Science* 262, 117-119 (1993).
8. Frank, K. M., et al. Investigation of the cause of death in a gene-therapy trial. *N. Engl. J. Med.* 361, 161-169 (2009).
9. Woods, N. B., Bottero, V., Schmidt, M., von Kalle, C. & Verma, I. M. Gene therapy: therapeutic gene causing lymphoma. *Nature* 440, 1123 (2006).
10. Patil, S. D., Rhodes, D. G. & Burgess, D. J. DNA-based therapeutics and DNA delivery systems: a comprehensive review. *AAPSJ* 7, E61-77 (2005).
11. Yoo, J. W., Irvine, D. J., Discher, D. E. & Mitragotri, S. Bio-inspired, bioengineered and biomimetic drug delivery carriers. *Nat Rev Drug Discovery* 10, 521-535 (2011).
12. Petros, R. A. & DeSimone, J. M. Strategies in the design of nanoparticles for therapeutic applications. *Nat. Rev. Drug Discov.* 9, 615-627 (2010).
13. De, M., Ghosh, P. S. & Rotello, V. M. Applications of Nanoparticles in Biology. *Adv Mater* 20, 4225-4241 (2008).
14. Davis, M. E., Chen, Z. G. & Shin, D. M. Nanoparticle therapeutics: an emerging treatment modality for cancer. *Nat Rev Drug Discovery* 7, 771-782 (2008).
15. Li, S. D. & Huang, L. Gene therapy progress and prospects: non-viral gene therapy by systemic delivery. *Gene. Ther.* 13, 1313-1319 (2006).
16. Mehier-Humbert, S. & Guy, R. H. Physical methods for gene transfer: improving the kinetics of gene delivery into cells. *Adv. Drug Deliv Rev* 57, 733-753 (2005).
17. Wu, T. H., et al. Photothermal nanoblade for large cargo delivery into mammalian cells. *Anal. Chem.* 83, 1321-1327 (2011).
18. Scheiblhofer, S., et al. Gene gun immunization with clinically relevant allergens aggravates allergen induced pathology and is contraindicated for allergen immunotherapy. *Mol. Immunol.* 44, 1879-1887 (2007).
19. Boukany, P. E., et al. Nanochannel electroporation delivers precise amounts of biomolecules into living cells. *Nat. Nanotechnol.* 6, 747-754 (2011).
20. Donahue, R. E., et al. Stimulation of haematopoiesis in primates by continuous infusion of recombinant human GM-CSF. *Nature* 321, 872-875 (1986).
21. Hernot, S. & Klibanov, A. L. Microbubbles in ultrasound-triggered drug and gene delivery. *Adv Drug Deliv Rev* 60, 1153-1166 (2008).
22. Wang, S., et al. Three-dimensional nanostructured substrates toward efficient capture of circulating tumor cells. *Angew Chem Int Ed Engl* 48, 8970-8973 (2009).
23. Peng, K. Q., Yan, Y. J., Gao, S. P. & Zhu, J. Synthesis of large-area silicon nanowire arrays via self-assembling nanoelectrochemistry. *Adv Mater* 14, 1164-1167 (2002).
24. Chen, K. J., et al. The therapeutic efficacy of camptothecin-encapsulated supramolecular nanoparticles. *Biomaterials* 33, 1162-1169 (2012).
25. Liu, Y., et al. Delivery of intact transcription factor by using self-assembled supramolecular nanoparticles. *Angew Chem Int Ed Engl* 50, 3058-3062 (2011).
26. Chen, K. J., et al. A small MRI contrast agent library of gadolinium(III)-encapsulated supramolecular nanoparticles for improved relaxivity and sensitivity. *Biomaterials* 32, 2160-2165 (2011).
27. Wang, S., et al. Photothermal effects of supramolecularly assembled gold nanoparticles for the targeted treatment of cancer cells. *Angew Chem Int Ed Engl* 49, 3777-3781 (2010).
28. Wang, H., et al. A rapid pathway toward a superb gene delivery system: programming structural and functional diversity into a supramolecular nanoparticle library. *ACS Nano* 4, 6235-6243 (2010).
29. Wang, H., et al. A small library of DNA-encapsulated supramolecular nanoparticles for targeted gene delivery. *Chem Commun (Camb)* 46, 1851-1853 (2010).
30. Wang, H., et al. A supramolecular approach for preparation of size-controlled nanoparticles. *Angew Chem Int Ed Engl* 48, 4344-4348 (2009).
31. Sekine, J., et al. Functionalized conducting polymer nanodots for enhanced cell capturing: the synergistic effect of capture agents and nanostructures. *Adv Mater* 23, 4788-4792 (2011).
32. Fischer, K. E., et al. Biomimetic nanowire coatings for next generation adhesive drug delivery systems. *Nano Lett* 9, 716-720 (2009).
33. Zhang, S., Li, J., Lykotrafitis, G., Bao, G. & Suresh, S. Size-Dependent Endocytosis of Nanoparticles. *Adv Mater* 21, 419-424 (2009).
34. Jaiswal, J. K., Goldman, E. R., Mattoussi, H. & Simon, S. M. Use of quantum dots for live cell imaging. *Nat Methods* 1, 73-78 (2004).
35. Kim, W., Ng, J. K., Kunitake, M. E., Conklin, B. R. & Yang, P. Interfacing silicon nanowires with mammalian cells. *J Am Chem Soc* 129, 7228-7229 (2007).
36. Shalek, A. K., et al. Vertical silicon nanowires as a universal platform for delivering biomolecules into living cells. *Proc Natl Acad Sci USA* 107, 1870-1875 (2010).
37. Pfisterer, U., et al. Direct conversion of human fibroblasts to dopaminergic neurons. *Proc Natl Acad Sci USA* 108, 10343-10348 (2011).
38. Vierbuchen, T., et al. Direct conversion of fibroblasts to functional neurons by defined factors. *Nature* 463, 1035-1041 (2010).

Example II—Supplementary Information

A. General

Reagents and solvents were purchased from Sigma-Aldrich (St. Louis, Mo.) and were used as received without further purification otherwise noted. (100) Oriented Silicon wafers (p-type, resistivity of ca. 10-20 Ωcm) were obtained from Silicon Quest Int. 2-well Lab-Tek™ Chamber Slides were purchased from Thermo Fisher Scientific. Branched polyethylenimine (PEI, MW=10 kD) was purchased from Polysciences Inc. (Washington, Pa.). Polymers contain primary, secondary, and tertiary amine groups in approximately 25/50/25 ratio. 1st-generation polyamidoamine dendrimer (PAMAM) with 1,4-diaminobutane core and amine terminals in a 20% wt methanol solution was purchased from Dendritic Nanotechnologies, Inc (Mount pleasant, MI). 1-Adamantanamine (Ad) hydrochloride and β-cyclodextrin (β-CD) were purchased from TCI America (San Francisco, Calif.). Phosphate-buffered saline (PBS, 1×, pH 7.2±0.05) used for sample preparation. 6-Mono-tosyl-β-cyclodextrin (6-OTs-β-CD) was prepared following the literature recommended method[1]. Octa-Ad-grafted polyamidoamine dendrimer (Ad-PAMAM), CD-grafted branched polyethylenimine (CD-PEI) and Ad-grafted polyethylene glycol (Ad-PEG) were prepared by the same methods reported previously[2]. Dry $CH_2Cl_2$ was obtained by refluxing over $CaH_2$ and freshly distilled before use. NIH 3T3 (mouse embryonic fibroblast cell line), U87 (human brain glioblastoma cell line), HeLa (human cervix epithelial carcinoma cells), MCF7 (human breast adenocarcinoma cells), HEK293 (human embryonic kidney cells), BC-1 (lymphoma cells), Ramos (Human Burkitt's lymphoma cells) and Jurkat (Human T cell lymphoblast-like cells) were purchased from American Type Culture Collection (ATCC). The Dulbecco's Modified Eagle Medium (DMEM), Earl's Modified Eagle's Medium (EMEM) growth medium and Penicillin/streptomycin were obtained from Invitrogen (Carlsbad, Calif.). Fetal Bovine Serum (FBS) and EGFP-encoded plasmid (pMAX EGFP®, 4.3 kb) were obtained from Lonza Walkerrsville Inc. (Walkerrsville, Md.). mCherry-encoded plasmid (4.7 kb) and E2-Crimson-encoded plasmid (4.6 kb) were purchased from Clontech Laboratories Inc. (Mountain View, Calif.). EGFP-siRNA was obtained from Invitrogen (Carlsbad, Calif.). Cy5™ monofunctional dye (Cy5-NHS) was purchased from GE Healthcare. Transcription factor, GAL4-VP16, was purchased from Jena Bioscience (Jena, Germany). CellTitra Blue cell viability kit was purchased from Promega (Madison, Wis.).

Dynamic light scattering of biomolecules ⊂ SNPs were measured on Zetasizer Nano instrument (Malvern Instruments Ltd., United Kingdom). Transmission electron microscope (TEM) images were measured on Philips CM 120 electron microscope operating with an acceleration voltage of 120 kV. Cell imaging, gene transfection and protein transduction studies were performed on a Nikon TE2000S inverted fluorescent microscope with a cooled charge-coupled device (CCD) camera (QImaging, Retiga 4000R), X-Cite 120 Mercury lamp, automatic stage, and filters for three fluorescent channels (W1 (EGFP), W2 (mCherry) and W3 (Cy5)). Fluorescence and bioluminescence intensities were measured by a Fujifilm BAS-5000 microplate reader. Bioluminescence images were acquired using a CCD camera (IVIS, Xenogen).

B. Dynamic Light Scattering (DLS)

DLS experiments were performed with a Zetasizer Nano instrument (Malvern Instruments Ltd., United Kingdom) equipped with a 10-mW helium-neon laser ($\lambda$=632.8 nm) and a thermoelectric temperature controller. Measurements were taken at a 90° scattering angle. The hydrodynamic size of the biomolecules ⊂ SNPs were measured by using DLS. The sizes and the standard derivations were obtained by averaging the values of three or more measurements.

C. Transmission Electron Microscope (TEM)

The morphology and sizes of Ad-SiNW and DNA ⊂ SNPs enriched Ad-SiNW were examined using a transmission electron microscope. The studies were carried out on a Philips CM 120 electron microscope, operating at an acceleration voltage of 120 kV. The TEM samples were prepared by drop-coating 2 μL of sample suspension solutions onto carbon-coated copper grids. Excess amounts of solution were removed by filter papers after 45 s. Subsequently, the samples were negatively stained with 2% uranyl acetate for 45 s before TEM studies.

D. Scanning Electron Microscopy (SEM)

We prepared samples of the cell-attached substrate for SEM observation by a standard procedure: Briefly, the U87 cells were cultured on Ad-SiNW overnight to ensure their settlement onto Ad-SiNWS. DNA ⊂ SNPs were then added to the medium, and the resulting solution was incubated for 20 min at 37° C. (5% $CO_2$). The cells were washed with PBS twice and fixed with 4% glutaraldehyde solution (4° C., 1 hr). Cells were then post-fixed in 1% osmium tetroxide for 1 h, and 1% tannic acid was used as a mordant. Samples were dehydrated through a series of alcohol concentrations (30%, 50%, 70% and 90%), stained in 0.5% uranyl acetate, and followed by further dehydration (96%, 100% and 100% alcohol). The final dehydration was in hexamethyldisilazane (HMDS), followed by air drying. Once dry, the samples were sputter coated with gold before examination with a Hitachi S800 field emission SEM at an accelerating voltage of 10 keV.

E. Microscope Settings, Imaging Processing and Data Analysis

The CDNS chip was mounted onto a Nikon TE2000S inverted fluorescent microscope with a CCD camera (QImaging, Retiga 4000R), X-Cite 120 Mercury lamp, automatic stage, and filters for three fluorescent channels (W1 (EGFP), W2 (mCherry) and W3 (Cy5)). Following image acquisition, MetaMorph (Molecular Devices, Version 7.5.6.0) was used to quantify the cells' EGFP expression, and their mCherry and Cy5 fluorescence intensity. The Multi-Wavelength Cell Scoring module of the Metamorph software allows for image analysis. A cell counting application in the module allowed us to calculate the total number of cells. In order to determine the gene transfection efficiency, the EGFP-expressed cells were counted by the MetaMorph program, which distinguishes the transfected cells from the non-transfected cells. The EGFP fluorescence intensity of non-transfected cells are 200~300 pixels higher than the background. Cells with an EGFP fluorescence intensity 300 pixels higher than the background are recognized as transfected cells. The gene transfection efficiency was defined as the EGFP-expressed cell number divided by the total cell number. The protein transduction efficiency was quantified by the fluorescence intensities of fluorophores labeled in the proteins of the transduced cells.

F. Cell Viability Assay

Figure 6:
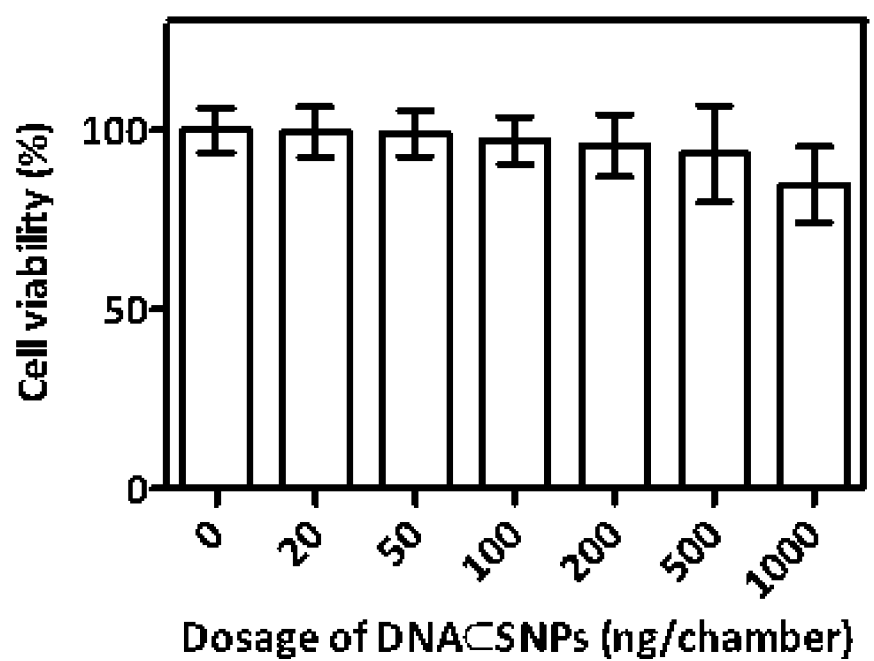
FIG. 6 shows cell viability on the CDNS platform, assessed by the MTT assay. Different dosages of 100-nm DNA ⊂ SNPs were used to treat the U87 cells for 24 h for MTT assay. Error bars are obtained from triplicate experiments.

The dosage-dependent cell viability on the CDNS platform was assessed by the MTT assay. U87 ($5\times10^4$ cells/chamber) cells were seeded into a 2-well chamber slide containing Ad-SiNWS, and 100-nm DNA ⊂ SNPs with different concentrations of plasmids were added into the culture medium and incubated with cells for 24 h. After incubation, CellTiter-Blue (100 μL) was added into each well and incubated for 3 h. The chamber slide was then placed on a shaking table (150 rpm for 5 min) to thoroughly mix the solution, and then fluorescence intensities were measured with excitation at 535 nm and emission at 585 nm. As shown in FIG. 6, there were no significant fluorescence intensity differences between the treated and non-treated cells, which suggested negligible cell disruption caused by CDNS platform.

G. Time-dependent transduction of DNA ⊂ SNPs into cells on different substrates

Figure 7:
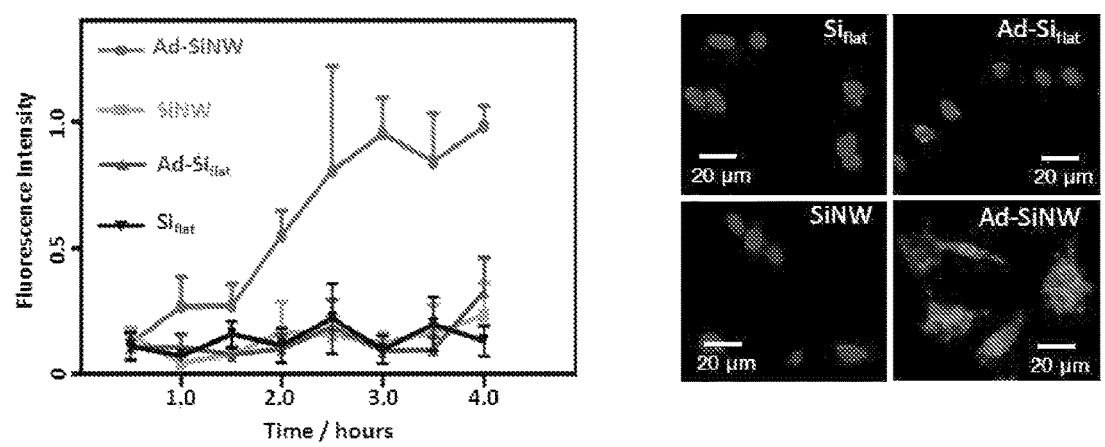
FIG. 7 shows time-dependent Cy5 labeled DNA ⊂ SNPs uptake by U87 cells on different silicon substrates including Ad-SiNWS, SiNW, Ad-Siflat and Siflat substrates (left). Error bars are obtained from triplicated experiments. Fluorescence micrographs of the Cy5 labeled DNA ⊂ SNPs uptake by U87 on different silicon substrates for 4 h (right). The cell nuclei were stained with DAPI.

In order to understand the dynamics of DNA ⊂ SNP transduction into cells on different substrates, we employed real-time fluorescence microscopy to monitor the uptake of Cy5 labeled DNA ⊂ SNPs by U87 cells. The DNA ⊂ SNPs grafted onto the Ad-SiNWS showed the highest cell-uptake efficiency compared to the other three substrates (i.e., silicon nanowire (SiNW), Ad-grafted flat silicon (Ad-Siflat) and flat silicon (Siflat)). The fluorescence intensity, reflecting the quantity of the Cy5 labeled DNA ⊂ SNPs by cells, was saturated ca. 3-4 h (FIG. 7, left). The typical fluorescence micrographs of the Cy5 labeled DNA ⊂ SNPs uptake by U87 cells for 4 h were showed in FIG. 7 (right).

H. Interface Between CDNS Platform and Cells

Figure 8:
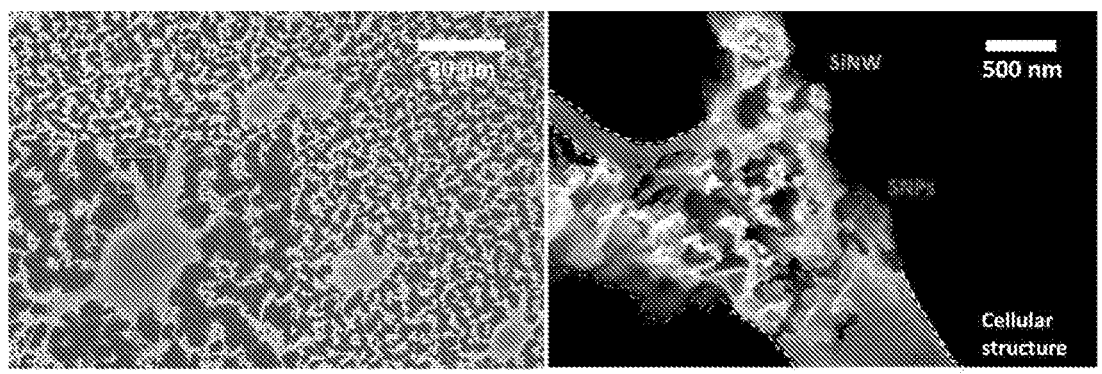
FIG. 8 shows the interface between CDNS platform and cells (U87). SEM investigation shows that the cell settled on the DNA ⊂ SNPs locally enriched Ad-SiNWS as predicted. The typical interface area in the left panel was highlighted with an orange rectangle and enlarged in the right panel. The cellular structure (white dotted lines), SiNW (blue dotted lines), and SNPs (red arrows) interact topographically.

To gain insight into the catalytic mechanism of CDNS platform, we investigated the interface properties between CDNS platform and cells. As seen in FIG. 8, observation of many interdigitated cellular protrusions (with diameters of about 100-200 nm) on the DNA⊂SNPs enriched Ad-SiNWS validates the enhanced topographic interactions between cells and CDNS platform.

I. General Information Regarding EGFP, mCherry and E2-Crimson Encoded Plasmids

EGFP-encoded plasmid (pMAX EGFP®, 4.3 kb), mCherry-encoded plasmid (4.7 kb) and E2-Crimson-encoded plasmid (4.6 kb) driven by CMV promoters. EGFP, mCherry and E2-Crimson proteins expressed cells can be detected by fluorescence microscopy at an emission maximum of 510, 610, 646 nm. In order to determine the continuous delivery capability of CDNS platform, U87 cells were sequentially treated with three different SNP vectors with encapsulated DNA plasmids (specifically encoding EGFP, mCherry and E2-Crimson) at 12 h, 24 h and 36 h post cell settlement. Individual fluorescent protein delivery efficiencies were calculated and are shown in FIG. 3g.

J. Construction of pG5E4T-Fluc Vector and GAL4-VP16 Activity Assay pG5E4T-Fluc plasmid was prepared according to a literature procedure: Briefly, five copies of 17-bp GAL4 binding sites were placed on 23-base upstream of the TATA box of the E4 gene of adenovirus (G5E4T)[3]. Then, this G5E4T sequence was amplified via PCR with primers to attach SacI and XhoI sites on up- and down-streams, respectively. Finally, the pG5E4T-Fluc plasmid was constructed by digesting SacI and XhoI sites of PCR-amplified fragments and introducing them into pGL3-Basic vector (Promega).

In order to determine the GAL4-VP 16 activity after delivery, we quantified the luciferase expression by measuring the bioluminescence intensity of U87 cells treated by CDNS platform. GAL4-VP16 encapsulated SNPs were prepared using the previously described method. U87 cells were seeded into each of a 2-well chamber slide containing the Ad-SiNW substrates the day before exposure to the GAL4-VP16 encapsulated SNPs and control groups (PBS). Cells were incubated for 24 h to allow for the luciferase expression that was activated by GAL4-VP16. To quantify the luciferase expression, cells were lysed and the cell lysate was transferred to a 96-well plate. Then, 100-µL luciferin substrate (Promega, E1500) was added to each well and the resulting solution was incubated at room temperature for 2 min. Bioluminescence intensities were then measured by both the micro plate reader (Fujifilm BAS-5000) and the CCD camera (IVIS, Xenogen).

K. Generation of Induced Neuronal Like (iNl) Cells from Fibroblast Cells

1. General

Mouse MEF fibroblast cell line, human BJ, and HDF foreskin fibroblast cells were obtained from ATCC. Cells were then cultured in Dulbecco's modified Eagle's medium (DMEM) supplemented with 10% FBS, 100 units/ml penicillin, and 100 µg/ml streptomycin. Plasmids designed for transdifferentiation were generated (and are described previously[4,5]). Plasmids #27150 (Tet-O-FUW-Ascl1), #27151 (Tet-O-FUW-Brn2), #27152 (Tet-O-FUW-Myt1l), #30129 (Tet-O-FUW-NeuroD1), #19780 (FUdeltaGW-rtTA) were obtained from Addgene. During the treatment of fibroblast cells with pNTFs⊂SNPs using CDNS, the Mouse MEF fibroblast cells were cultured in the mixture of Neurobasal medium and DMEM/F12 (1:1) supplemented with 1% B27, 1% Glutamine, 0.5% N2, 3.4 L β-mercaptomethanol, 100 units/ml penicillin, and 100 µg/ml streptomycin. For treatment of human fibroblast cell lines, cells were cultured in DMEM/F12 supplemented with 1% B27, 1% Glutamine, 100 units/ml penicillin, and 100 µg/ml streptomycin.

2. Immunofluorescence Staining of Multiple Neuron-Specific Proteins

Cell cultures were fixed at different time intervals after treatment. Cells were first washed three times in PBS, fixed in 4% paraformaldehyde solution in PBS for 10 min at room temperature, and then washed again three times with PBS. Prior to immunochemical staining, the cells were incubated for 30 min in TNBS (PBS supplemented with 0.4% Triton-X 100 and 5% normal goat serum) to improve their permeability. Cells were then incubated at 4° C. overnight in TNBS (PBS supplemented with 5% normal goat serum) containing the primary antibodies: Tuj1 (Covance, 1:500), Map2 (Sigma, 1:200), NeuN (Millipore, 1: 200), Nestin (Santa Cruz, 1:200). After washing twice with TNBS for 5 min, cells were incubated in PBS containing the secondary antibodies: Goat anti-mouse Cy3 and Goat anti-rabbit Cy2 (Jackson ImmunoResearch, 1:500). After another wash with TNBS, cells were stained with Hoechst 33342 in a final concentration of 5 µg/ml for 10 min. After washing again with TNBS, a droplet of Vectashield (Molecular Probes) was placed on top of the stained cells and the cells were covered with a coverslip.

3. Time-Dependent Expression for Neuron-Specific Protein of iNl Cells.

Figure 9:
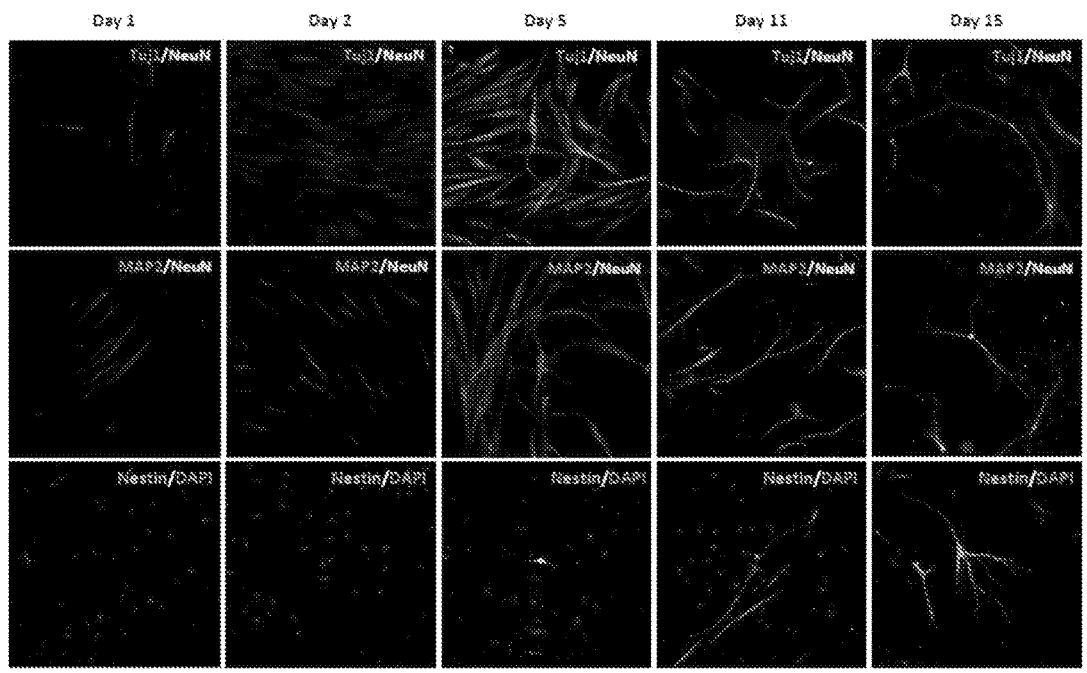
FIG. 9 shows immunofluoroscence staining of neuron-specific proteins including Tuj1, Map2, NeuN and Nestin at different days during the treatment of HDF using CDNS.

In order to gain insight into how fibroblasts (HDF) were converted into iNl cells, we monitored the expression of several neuronal genes during the fibroblast-iNl cell conversion at Day1, Day2, Day5, Day11 and Day15. Briefly, the plated cells were fixed on Ad-SiNWS and immunofluorescence staining of neuron-specific markers including Tuj1, Map2, NeuN and Nestin were performed to determine the neuron cell identity. From the results indicated in FIG. 9, at Day11 and Day15, the treated cells showed obvious neuron-specific protein expression and morphology change. Therefore, Day11 and Day15 were selected as the two time points to evaluate the conversion performance.

REFERENCES

1. Petter, R. C., Salek, J S, Sikorski C T, Kumaravel G, Lin F T. Cooperative Binding by Aggregated Mono-6-(Alkylamino)-Beta-Cyclodextrins. JACS 112(10). (1990): 3860-3868.
2. Wang, H., Wang, S. T., Su, H., Chen, K. J., Armijo, A. L., Lin, W. Y., et al. A Supramolecular Approach for Preparation of Size-Controlled Nanoparticles. Angew Chem Int Ed. 2009; 48(24):4344-8.
3. Iyer, M., Wu, L., Carey, M., Wang, Y., Smallwood, A., Gambhir, S. S. Two-step transcriptional amplification as a method for imaging reporter gene expression using weak promoters. P Natl Acad Sci USA. 2001; 98(25):14595-600.
4. Vierbuchen, T., Ostermeier, A., Pang, Z. P., Kokubu, Y., Sudhof, T. C., Wernig, M. Direct conversion of fibroblasts to functional neurons by defined factors. Nature. 463 (7284):1035-41.
5. Pfisterer, U., Kirkeby, A., Torper, O., Wood, J., Nelander, J., Dufour, A., et al. Direct conversion of human fibroblasts to dopaminergic neurons. Proc Natl Acad Sci USA. 108(25):10343-8.

From the forgoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional application 61/510,263, filed Jul. 21, 2011, and in the figures, are hereby incorporated by reference in their entirety, particularly with regard to the specific findings for which they are referenced herein.

We claim:

1. A molecular delivery system, comprising:
   a substrate having
   a nanostructured surface region which comprises a plurality of nanostructures and, covalently attached to the nanostructured surface region, multiple copies of a first member of a binding pair; and
   at least one vector nanoparticle which comprises encapsulated therein, a molecule of interest, and, on its surface, multiple copies of a second member of the binding pair,
   wherein the plurality of nanostructures are nanofibers or nanowires made of silicon, titanium, aluminum, steel, or an organic oxide, or are organic polymers comprising at least one of polymethacrlate, polysaccharide or polylactide,
   wherein the plurality of nanostructures comprise a length and diameter such that the length is greater than the diameter,
   wherein the plurality of nanostructures are attached at a first end to the substrate, and
   wherein the first member of the binding pair is covalently attached to an outer surface region of the plurality of nanostructures such that the at least one vector nanoparticle is attached to the outer surface region of the plurality of nanostructures when the second member of the binding pair and the first member of the binding pair are engaged, and
   wherein each vector nanoparticle further comprises:
   a plurality of structural components that are suitable to at least provide some mechanical structure to said vector nanoparticle;
   a plurality of binding components, each having a plurality of binding regions adapted to bind to said plurality of structural components; and
   a plurality of terminating components, each of which is adapted to bind to a binding region of one of said plurality of binding components,
   wherein said plurality of structural components and said plurality of binding components self-assemble when brought into contact to form said vector nanoparticle,
   wherein said plurality of terminating components act to occupy binding regions of said plurality of binding components to terminate further binding when said plurality of terminating components are present in a sufficient quantity relative to said plurality of binding regions of said plurality of binding components,
   wherein the plurality of binding regions comprise β-cyclodextrin,
   wherein each of said plurality of structural components comprises at least one binding element adapted to bind to the binding regions to form a first inclusion complex,
   wherein the binding element comprises adamantine,
   wherein the first inclusion complex is adamantine-β-cyclodextrin,
   wherein each of the plurality of terminating components comprise a single terminating binding element that binds to remaining binding regions of one of said plurality of binding components by forming a second inclusion complex,
   wherein said terminating binding element comprises adamantine, and
   wherein said second inclusion complex is adamantine-β-cyclodextrin.

2. A method for delivering a molecule of interest into a cell, comprising
   contacting the cell with a substrate having a nanostructured surface region which comprises a plurality of nanostructures, wherein multiple copies of a first member of a binding pair are covalently attached to the nanostructured surface region, so that the cell is associated with the nanostructured surface region; then
   immobilizing on the nanostructured surface region with which the cell is associated at least one vector nanoparticle, wherein the vector nanoparticle encapsulates the molecule of interest and comprises, on its surface, multiple copies of a second member of the binding pair, so that the vector nanoparticle is internalized by the cell and the molecule of interest is released from the vector particle and is delivered to the cell,
   wherein the plurality of nanostructures are nanofibers or nanowires made of silicon, titanium, aluminum, steel, or an organic oxide, or are organic polymers comprising at least one of polymethacrlate, polysaccharide or polylactide,
   wherein the plurality of nanostructures comprise a length and diameter such that the length is greater than the diameter,
   wherein the plurality of nanostructures are attached at a first end to the substrate, and
   wherein the first member of the binding pair is covalently attached to an outer surface region of the plurality of nanostructures such that the at least one vector nanoparticle is attached to the outer surface region of the plurality of nanostructures when the second member of the binding pair and the first member of the binding pair are engaged, and
   wherein the vector nanoparticle further comprises:
   a plurality of structural components that are suitable to at least provide some mechanical structure to said vector nanoparticle;
   a plurality of binding components, each having a plurality of binding regions adapted to bind to said plurality of structural components; and
   a plurality of terminating components, each of which is adapted to bind to a binding region of one of said plurality of binding components,
   wherein said plurality of structural components and said plurality of binding components self-assemble when brought into contact to form said vector nanoparticle,
   wherein said plurality of terminating components act to occupy binding regions of said plurality of binding components to terminate further binding when said plurality of terminating components are present in a sufficient quantity relative to said plurality of binding regions of said plurality of binding components,
   wherein the plurality of binding regions comprise β-cyclodextrin,
   wherein each of said plurality of structural components comprises at least one binding element adapted to bind to the binding regions to form a first inclusion complex,
   wherein the binding element comprises adamantine, wherein the first inclusion complex is adamantine-β-cyclodextrin, wherein each of the plurality of terminating components comprise a single terminating binding element that binds to remaining binding regions of one of said plurality of binding components by forming a second inclusion complex, wherein said terminating binding element comprises adamantine, and wherein said second inclusion complex is adamantine-β-cyclodextrin.

3. The method of claim 2, further comprising delivering more of the molecule of interest or delivering a second molecule of interest into the cell, wherein the method further comprises, after the first molecule of interest is delivered to the cell, immobilizing on the nanostructured surface region with which the cell is associated at least one vector nanoparticle comprising multiple copies of the second member of the binding pair, wherein the vector nanoparticle encapsulates more of the first molecule or encapsulates a second molecule, so that the vector nanoparticle is internalized by the cell and the further molecule of interest is released from the vector nanoparticle and is delivered to the cell.

4. A delivery system of claim 1, wherein the plurality of nanostructures are silicon nanowires.

5. A delivery system of claim 1, wherein the vector nanoparticle is a liposome, self-assembled nanoparticle based on amphiphilic polymer, an inorganic nanoparticle, polymer-based nanoparticles, or a sol-gel nanoparticle.

6. The molecular delivery system of claim 1, wherein the plurality of terminating components each have a single binding element that binds to one of the binding regions.

7. A delivery system of claim 1, wherein the first and second members of the binding pair are antibody-antigen; protein-substrate; protein-inhibitor; protein-protein; a pair of complementary oligonucleotides; or an inclusion complex.

8. A delivery system of claim 1, wherein the molecule of interest is a nucleic acid, a protein, a polysaccharide, or a small molecule.

9. A method of claim 2, wherein the cell is a tissue culture cell, a primary cell, an immune cell, a stem cell, or a neuron.

10. A kit for delivering a molecule of interest into a cell, comprising in one container a substrate comprising a nanostructured surface region to which are covalently attached multiple copies of a first member of a binding pair; and in a second container, at least one vector nanoparticle encapsulating the molecule of interest and comprising on its surface multiple copies of a second member of the binding pair, wherein the first member of the binding pair is covalently attached to an outer surface region of the nanostructured surface region such that the at least one vector nanoparticle is attached to the outer surface region of the nanostructured surface region when the second member of the binding pair and the first member of the binding pair are engaged, wherein the vector nanoparticle further comprises:

a plurality of structural components that are suitable to at least provide some mechanical structure to said vector nanoparticle;

a plurality of binding components, each having a plurality of binding regions adapted to bind to said plurality of structural components; and a plurality of terminating components, each of which is adapted to bind to a binding region of one of said plurality of binding components, wherein said plurality of structural components and said plurality of binding components self-assemble when brought into contact to form said vector nanoparticle, wherein said plurality of terminating components act to occupy binding regions of said plurality of binding components to terminate further binding when said plurality of terminating components are present in a sufficient quantity relative to said plurality of binding regions of said plurality of binding components, wherein the plurality of binding regions comprise β-cyclodextrin, wherein each of said plurality of structural components comprises at least one binding element adapted to bind to the binding regions to form a first inclusion complex, wherein the binding element comprises adamantine, wherein the first inclusion complex is adamantine-β-cyclodextrin, wherein each of the plurality of terminating components comprise a single terminating binding element that binds to remaining binding regions of one of said plurality of binding components by forming a second inclusion complex, wherein said terminating binding element comprises adamantine, and wherein said second inclusion complex is adamantine-β-cyclodextrin.

11. A delivery system of claim 1, wherein said nanofibers or nanowires are between 50-500 nm in diameter.

12. A delivery system of claim 1, wherein said vector nanoparticle is between 50-500 nm in diameter.

13. The method of claim 2, wherein said vector nanoparticle is between 50-500 nm in diameter.

14. The kit of claim 10, wherein said vector nanoparticle is between 50-500 nm in diameter.

* * * * *